US012564822B2

(12) United States Patent
Nawarathna et al.

(10) Patent No.: US 12,564,822 B2
(45) Date of Patent: Mar. 3, 2026

(54) DEVICE FOR MANUFACTURE OF T-CELLS FOR AUTOLOGOUS CELL THERAPY

(71) Applicant: NDSU Research Foundation, Fargo, ND (US)

(72) Inventors: Dharmakeerthi Nawarathna, Fargo, ND (US); Logeeshan Velmanickam, Fargo, ND (US); Vidura Jayasooriya, Fargo, ND (US)

(73) Assignee: NDSU RESEARCH FOUNDATION, Fargo, ND (US)

( * ) Notice: Subject to any disclaimer, the term of this patent is extended or adjusted under 35 U.S.C. 154(b) by 1037 days.

(21) Appl. No.: 17/685,059

(22) Filed: Mar. 2, 2022

(65) Prior Publication Data

US 2022/0266214 A1 Aug. 25, 2022

Related U.S. Application Data

(63) Continuation-in-part of application No. 16/326,812, filed as application No. PCT/US2017/050493 on Sep. 7, 2017, now abandoned.

(60) Provisional application No. 62/384,809, filed on Sep. 8, 2016.

(51) Int. Cl.
| | |
|---|---|
| *B01J 19/08* | (2006.01) |
| *A61K 40/11* | (2025.01) |
| *A61K 40/31* | (2025.01) |
| *A61K 40/42* | (2025.01) |
| *C12M 1/00* | (2006.01) |
| *C12M 1/42* | (2006.01) |

(Continued)

(52) U.S. Cl.
CPC ............ *B01J 19/087* (2013.01); *A61K 40/11* (2025.01); *A61K 40/31* (2025.01); *A61K 40/4205* (2025.01); *A61K 40/4211* (2025.01);

*C12M 23/34* (2013.01); *C12M 35/02* (2013.01); *C12N 5/0636* (2013.01); *C12N 13/00* (2013.01); *C12N 2501/515* (2013.01)

(58) Field of Classification Search
None
See application file for complete search history.

(56) References Cited

U.S. PATENT DOCUMENTS

| | | | | |
|---|---|---|---|---|
| 2010/0068794 A1* | 3/2010 | Oh | ......................... | C12M 35/02 435/285.1 |
| 2016/0238558 A1* | 8/2016 | Minerick | ......... | G01N 27/44791 |

FOREIGN PATENT DOCUMENTS

| | | | | |
|---|---|---|---|---|
| CN | 101168724 A | * | 4/2008 | ............ C12M 23/20 |

OTHER PUBLICATIONS

Frenea et al. "Design of Biochip Microelectrode Arrays for Cell Arrangement." 2"d Annual International IEEE-EMBS Special Topic Conference on Microtechnologies in Medicine 8z Biology May 24, 2002, Madison, Wisconsin USA, pp. 140-143. (Year: 2002).*

(Continued)

*Primary Examiner* — William H. Beisner
(74) *Attorney, Agent, or Firm* — Stites & Harbison, PLLC; Mandy Wilson Decker

(57) ABSTRACT

The present invention relates to a device for a scalable biomanufacturing platform for the production of modified cells such as CAR-modified T-cells while eliminating on-target/off-tumor toxicity and decreasing the current production cost by 500 times (per treatment), and to attendant methods. The includes a first chamber for proliferating a population of cells and a second chamber for modifying the cells to express a desired T-cell receptor antigen.

32 Claims, 24 Drawing Sheets

(51) Int. Cl.
    *C12N 5/0783*        (2010.01)
    *C12N 13/00*        (2006.01)

(56)                References Cited

OTHER PUBLICATIONS

Huang et al. "Dielectrophoretic Cell Separation and Gene Expression Profiling on Microelectronic Chip Arrays." Anal. Chem. 2002, 74, 3362-3371. (Year: 2002).*
Minnikanti et al. "Microfluidic based contactless dielectrophoretic device: modeling and analysis." 32nd Annual International Conference of the IEEE EMBS Buenos Aires, Argentina, Aug. 31-Sep. 4, 2010, pp. 6506-6509. (Year: 2010).*

* cited by examiner

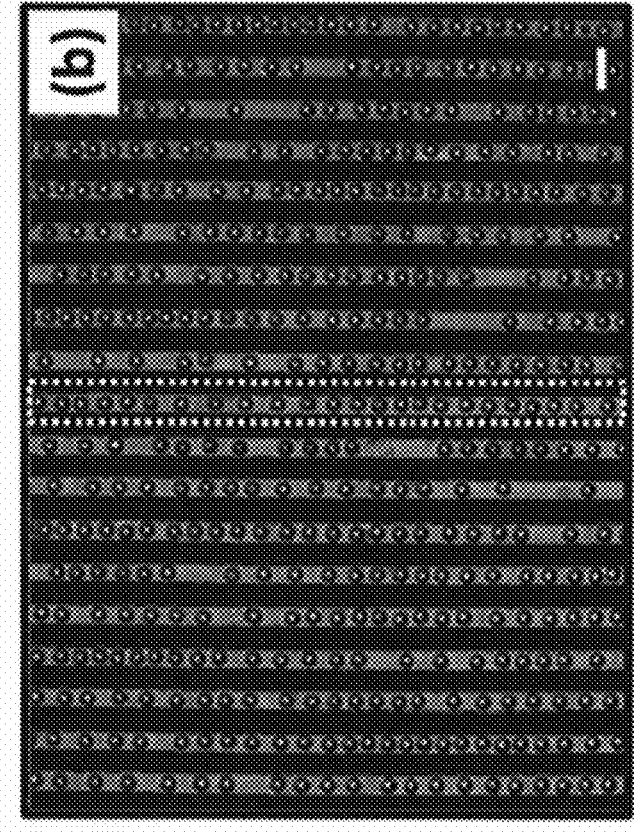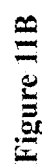
Figure 11B
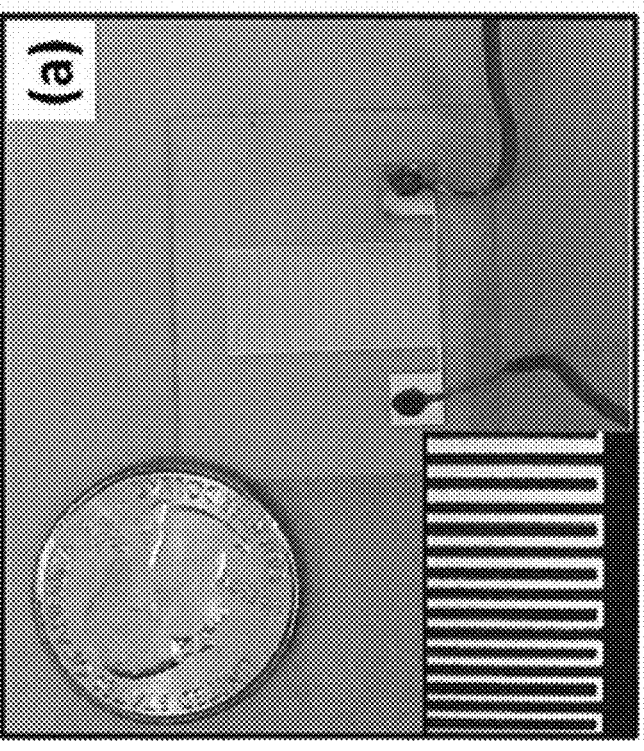
Figure 11A

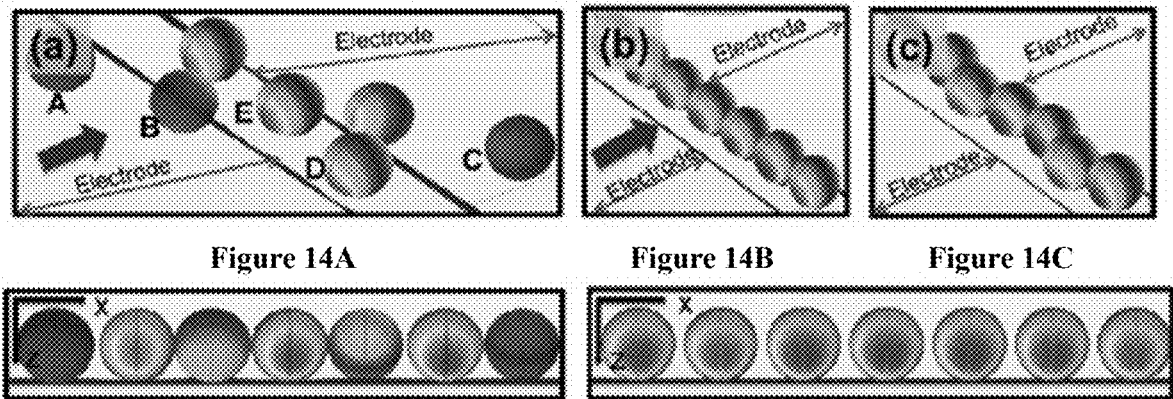
Figure 14A          Figure 14B          Figure 14C
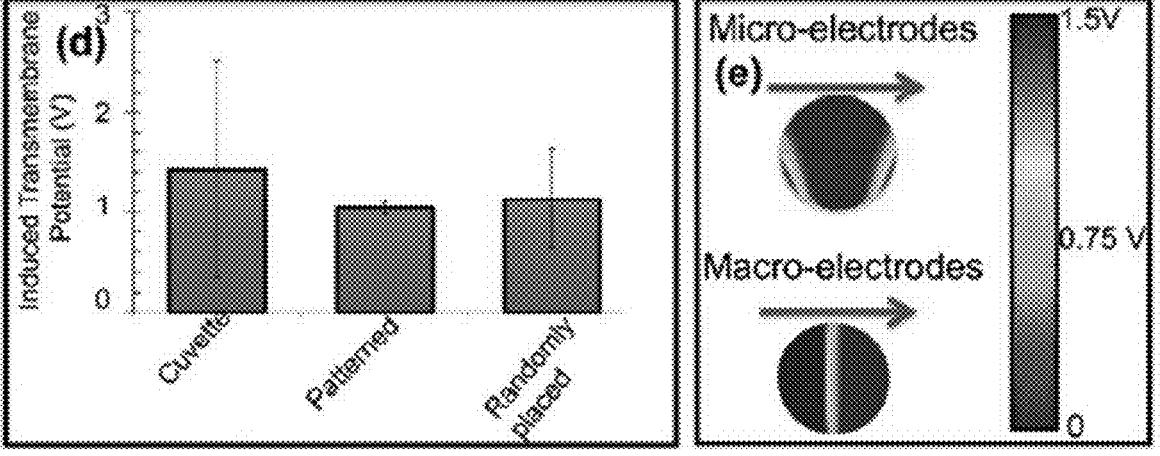
Figure 14D                    Figure 14E

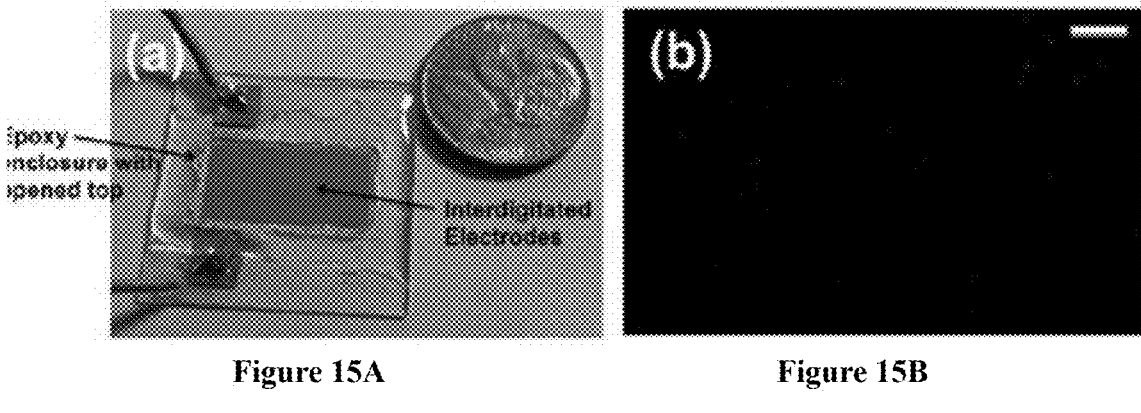
Figure 15A                                        Figure 15B
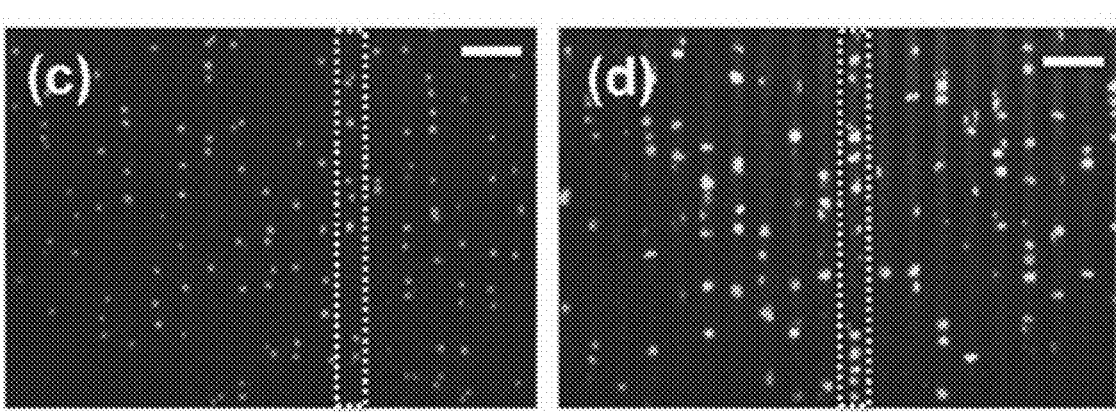
Figure 15C                                        Figure 15D

DEVICE FOR MANUFACTURE OF T-CELLS FOR AUTOLOGOUS CELL THERAPY

RELATED APPLICATIONS

This application is a continuation-in-part patent application claiming the benefit of priority in U.S. patent application Ser. No. 16/326,812 filed on Feb. 20, 2019, which is a national stage application of PCT/US2017/050493 filed on Sep. 7, 2017, which claims the benefit of U.S. Provisional Application Ser. No. 62/384,809, filed Sep. 8, 2016, the entire disclosures of each of which are incorporated herein by reference.

TECHNICAL FIELD

The presently-disclosed subject matter generally relates to devices and methods for the manufacture of CAR T-cells. In particular, certain embodiments of the presently-disclosed subject matter relate to devices and methods for the manufacture of CAR T-cells for autologous cell therapy.

BACKGROUND OF THE INVENTION

Cell-based therapies, especially Chimeric Antigen Receptors (CAR) T-cell therapy utilizing engineered T-cells expressing CARs, have shown a great potential to revolutionize the treatments for malignant tumors. As illustrated in FIG. 1, the current process includes collecting T-cells from a patient; multiplying the T-cells; reengineering the T-cells; and infusing a patient with the reengineered T-cells. More specifically, T-cells are collected from whole blood samples taken from a patient or via apheresis, a process that withdraws blood from the body and removes one or more blood components (such as plasma, platelets, or white blood cells). The remaining blood is then returned back into the body and the collected T-cells are multiplied or "expanded" by growing the cells in a laboratory to increase the number thereof. After multiplying the T-cells, they are sent to a laboratory or a drug manufacturing facility where they are genetically engineered to produce chimeric antigen receptors (CARs) on their surface. This can be by viral transfection or by inserting relevant mRNA into the cells. Following this reengineering, the T-cells are known as "chimeric antigen receptor (CAR) T-cells." CARs are proteins that allow the T-cells to recognize a specific antigen on targeted tumor cells. These CAR T cells are frozen and, when there are enough of them, they are sent to the hospital or center where the patient is being treated.

Some practitioners of CAR T-cell therapy vary the order of the multiplying and reengineering steps, particularly in view of whether the transfection occurs by viral transfection. For example, if expression of the desired CAR molecules is by insertion of mRNA into the cells, expansion of the cells after inserting mRNA into the T-cells would essentially dilute out the mRNA since it does not replicate. Therefore, some T-cells would not be able to express CAR molecules.

Regardless of the order in which the multiplying and reengineering steps are performed, once at the hospital or treatment center the CAR T cells are infused into the patient. Many patients are given a brief course of one or more chemotherapy agents before they receive the infusion of CAR T cells. CAR T cells that have been infused back to the patient's bloodstream multiply in number. These are the "attacker" cells that recognize, and kill, cancerous cells that have the targeted antigen on their surface. As the CAR T cells may remain in the body long after the infusion has been completed, they also guard against recurrence. Accordingly, the therapy frequently results in long-term remissions.

However, many obstacles still remain for CAR T-cell therapy. For example, although extensive research efforts have been continuing to develop CAR molecules targeting various tumors and subsequent analysis of efficacy, there has been no focus on developing manufacturing strategies that enable the production of CAR T-cells for therapy. For this reason, current production cost of a batch of CAR-modified T-cells for a single treatment is about $25,000. With therapies requiring up to 8-10 treatments, the total cost is typically at least about $200 k. Therefore, not only is the current process time consuming, it is expensive, and not widely available.

Additionally, the engineering of CAR modified T-cells is currently performed in a few centralized facilities using rudimentary biomanufacturing techniques, which result in heterogeneous mixtures of engineered CAR T-cells. These T-cells interact with nonpathogenic tissues and develop on-target/off tumor toxicity causing organ failures. As such, the current inability to manufacture homogenous mixtures of CAR expressing T-cells represents another significant hurdle to reengineered T-cell therapy. Thus, although CAR-based adoptive immunotherapy has the potential to revolutionize cancer treatments, these critical issues are hindering the translation of the latest developments in CAR T-cell biology into therapy.

One promising alternate approach to engineering T-cells with CAR receptors is through the transfection of T-cells with CAR producing mRNA using electroporation. Electroporation has been utilized to produce T-cells for cancer therapy targeting ErbB2 (Her2/neu) and CEA receptors in breast, pancreatic, lung and gastric cancers. In comparison with traditional viral-based transduction techniques, electroporation transiently expresses immunoreceptors (CAR) and therefore electroporation does not involve cellular genomic alteration, thereby eliminating adverse auto-aggression effects. However, this approach has not been previously achieved reliably, efficiently homogenously, or inexpensively.

This is due, in part, to the rudimentary nature of current two-electrode based electroporation techniques. As a result, controlled transfection of T-cells with mRNA molecules is not currently possible. This leads to the production of heterogeneous mixture of CAR modified T-cells causing these T-cells produce less than expected efficacy toward targeted cancer cells. This is creating a number of complex health issues leading to unnecessary consequences. Furthermore, the viability of cells after current T-cell electroporation is about 40%. The elimination of 60% of non-viable T-cells prior to treatments to avoid cross-reactions with other T-cells is technologically challenging because there are no distinct T-cell markers available for separation. These limitations in the current CAR modified T-cell production seriously undermine the true potential of adoptive immunotherapy.

Accordingly, there remains an urgent need for a viable engineering approach to cost-effectively produce CAR modified T-cells while minimizing the toxicity.

SUMMARY OF THE INVENTION

In some embodiments, the presently-disclosed subject matter relates to a device to produce modified T-cells comprising a first chamber for proliferating a population of T-cells and a second chamber for modifying the T-cells to express a desired chimeric receptor antigen or CAR.

In one embodiment, chamber 1 and chamber 2 comprise a top surface, a bottom surface and four sides, and two of the sides are essentially parallel to each other and are the ends and another two sides are essentially parallel and are the sides and the top and bottom surface are parallel to each other and are at a distance of about 100 μm from each other.

In one embodiment, the top and the side surfaces are made of PDMS and the bottom surface is made of glass. In another embodiment, chamber 1 includes a series of T-traps and chamber 2 includes one or more channels bordered on each side by a metal, wherein the metal on one side is connected to one electrode and the other side is connected to a second electrode. Metals may be selected from the group consisting of gold (Au), silver (Ag), platinum (Pt), copper (Cu), iron (Fe), aluminum (Al), Tin (Sn), Nickel (Ni), Carbon (C), doped silicon (Si), Indium tin oxide (ITO) or an alloy of metals.

In some embodiments, the electrical potential for chamber 1 is about 100 mVpp and for chamber 2 is about 1.5V/P, where the pulse is about 1 ms to about 10 ms to achieve electroporation.

Also provided herein, in some embodiments, is a kit comprising the device disclosed herein combined with one or more of the accessories selected from the group consisting of syringes, nutrients, food, cytokines, buffers, storage containers, transfer vehicles and instructions

4 after 24 hours (left) as compared to cells after electroporation (right). (B) Growth of electroporated cells after 48 hours (left) as compared to cells after electroporation (right). All images shown at 10× zoom.

Figure 9A:
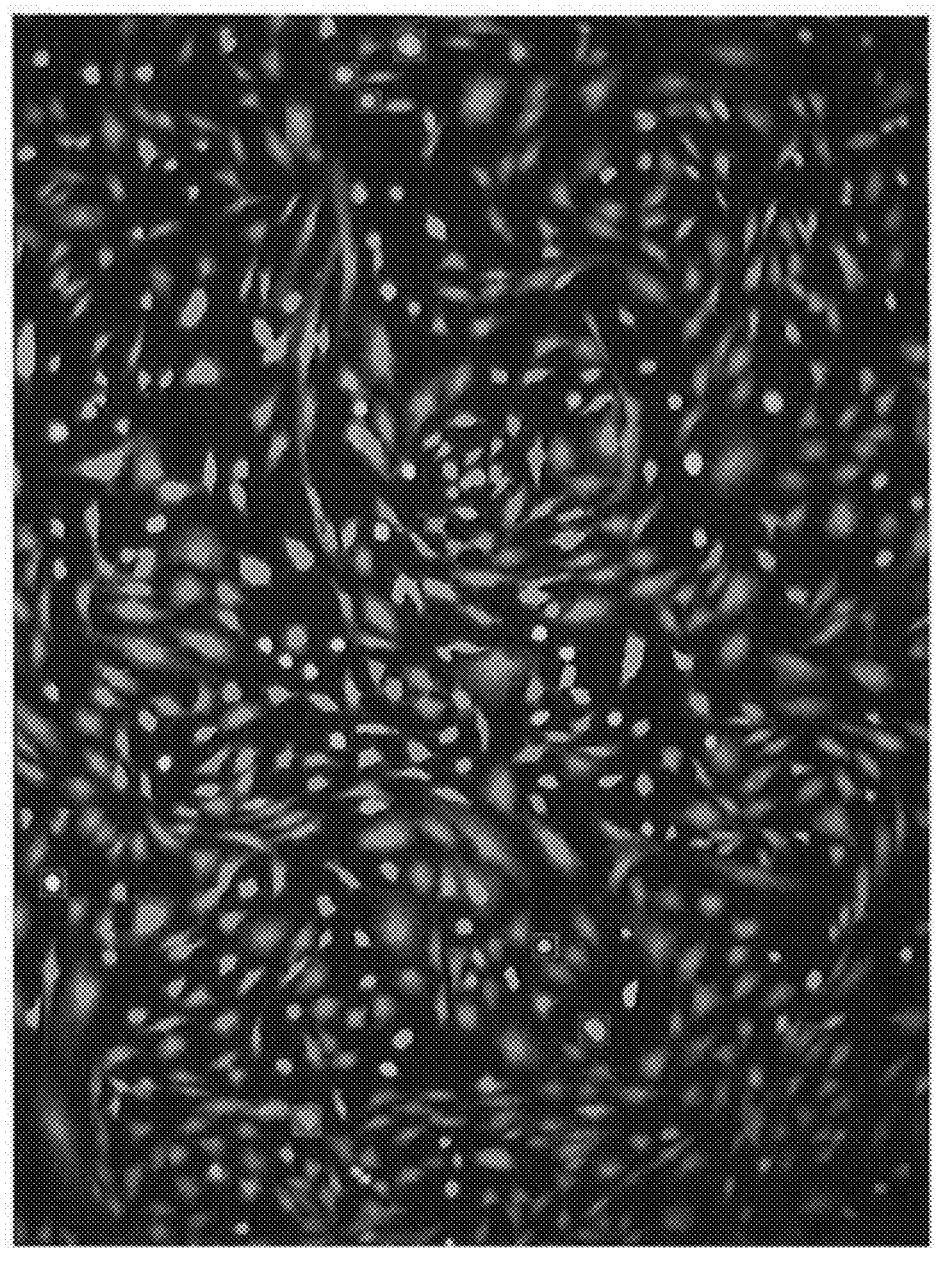
Figure 9B:
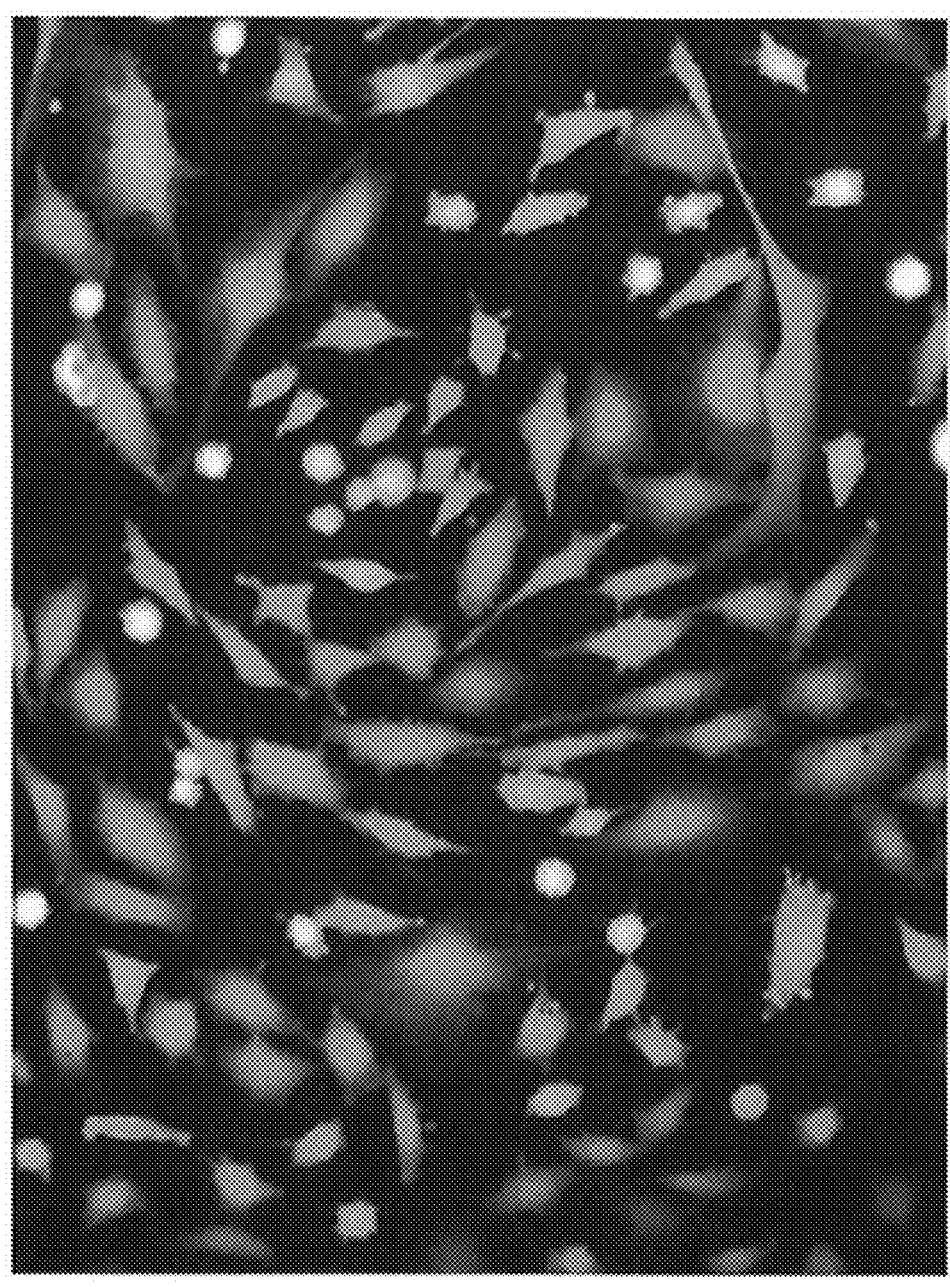

FIGS. 9A-B show images illustrating the cell viability after electroporation analyzed using Calcein staining. (A) 10× zoom image hours. (B) 25× zoom images.

Figures 10A, 10B, 10C:
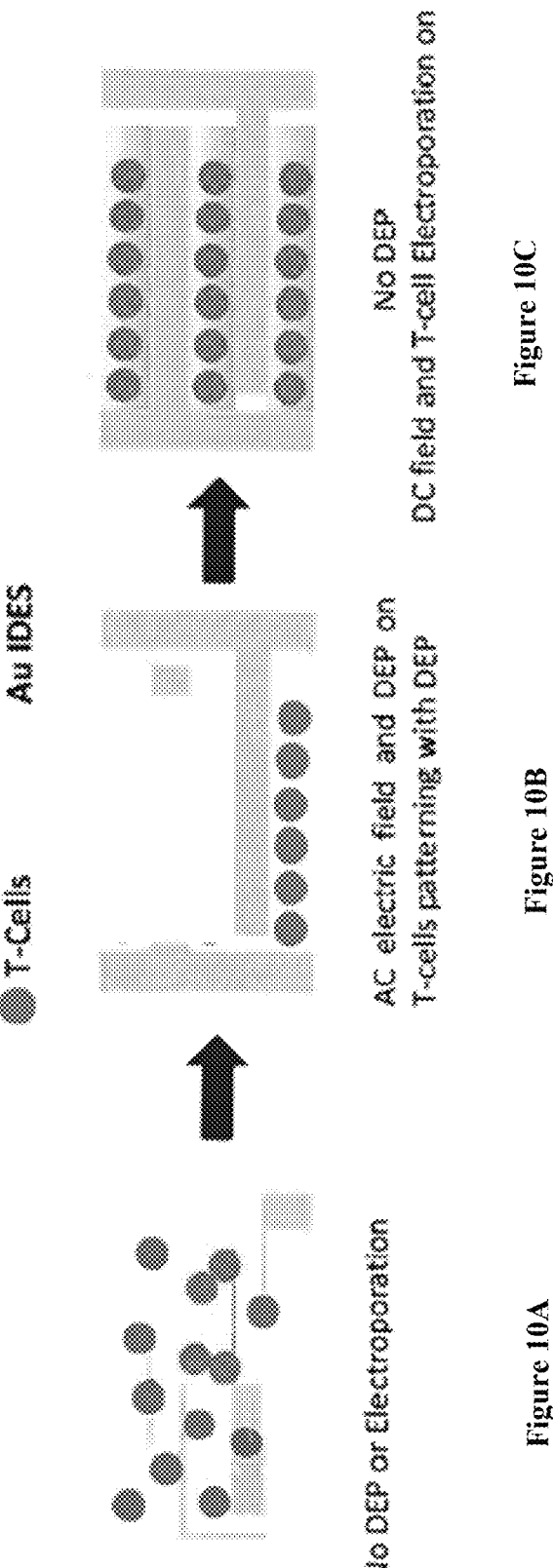

FIGS. 10A-C shows schematic diagram of the proposed CAR T-cell engineering by electroporation. (A) flow T-cells over interdigitated electrodes (IDEs), (B) T-cell patterning using DEP, (C) massively parallel electroporation of single T-cells. (A and B) T-cell purification and (A-C) transfection of T-cells with mRNA.

Figure 11C:
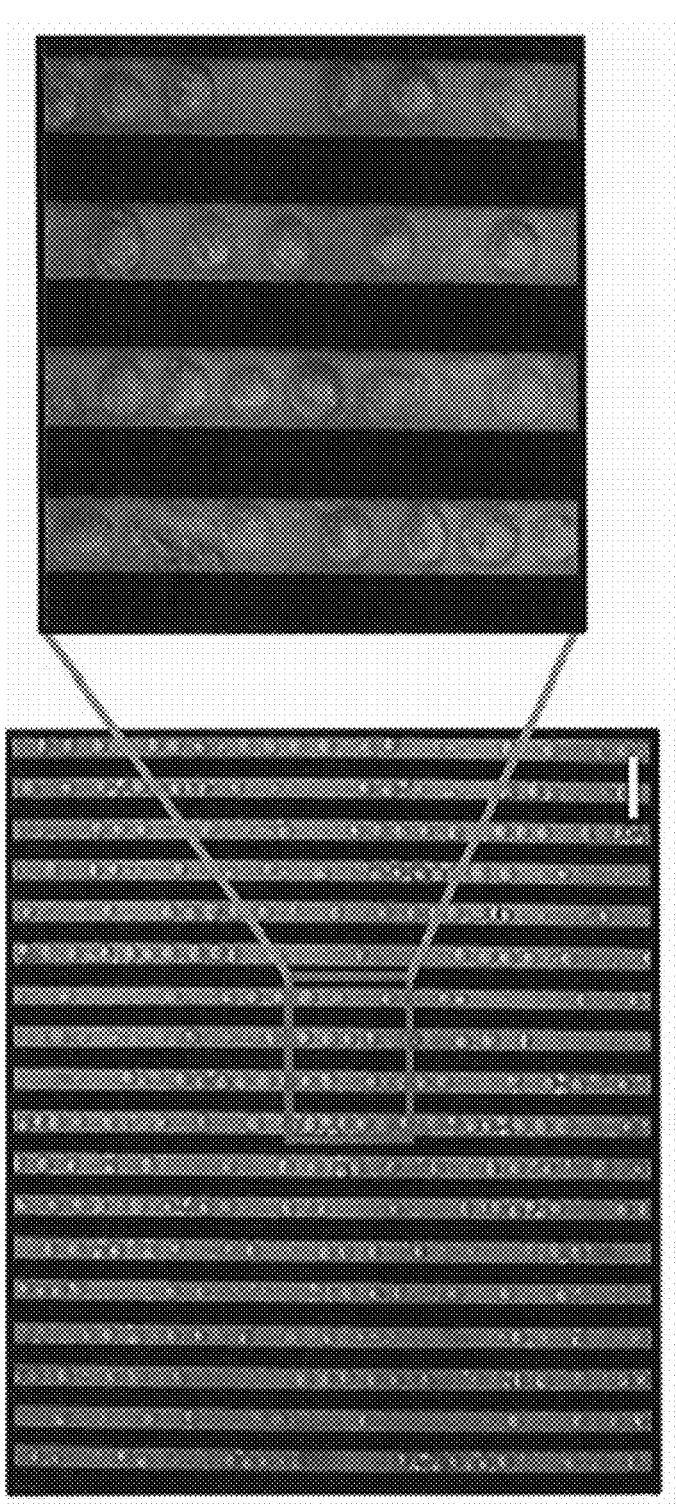

FIGS. 11A-C show the designed and fabricated IDE array for T-cell pattering and electroporation. (A) Picture of the fabricated IDE array and inset illustrate the close-up view of the individual IDE pairs. (B) Demonstration of the particle patterning using DEP. Polystyrene beads (diameter=10 μm) were trapped and patterned between individual IDEs using DEP. Rectangle with white broken lines shows perfectly aligned beads. (C) Patterning of fibroblast cells (CRL—1764) using DEP. Scale bars indicate 30 μm.

Figure 12A:
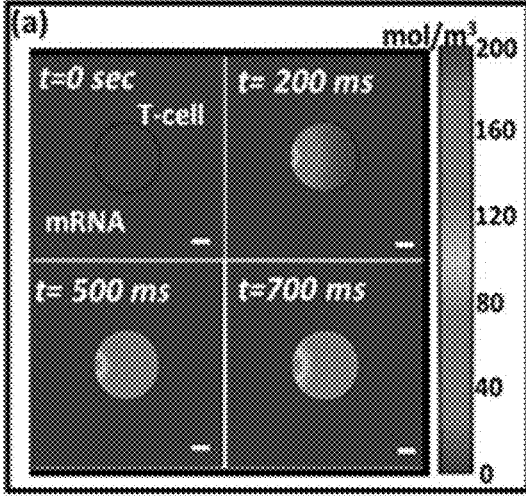
Figure 12B:
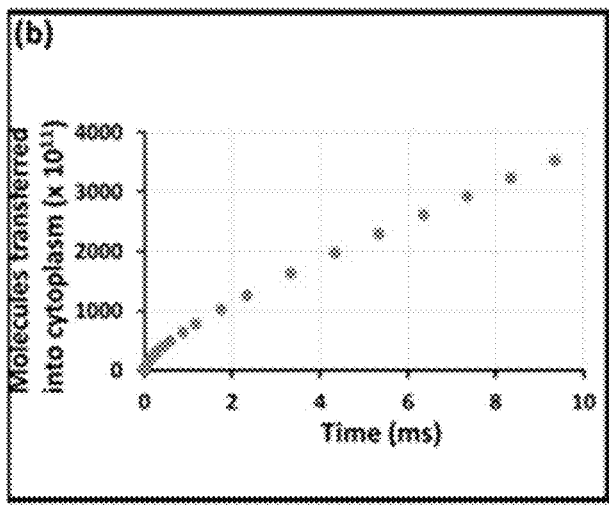
Figure 12C:
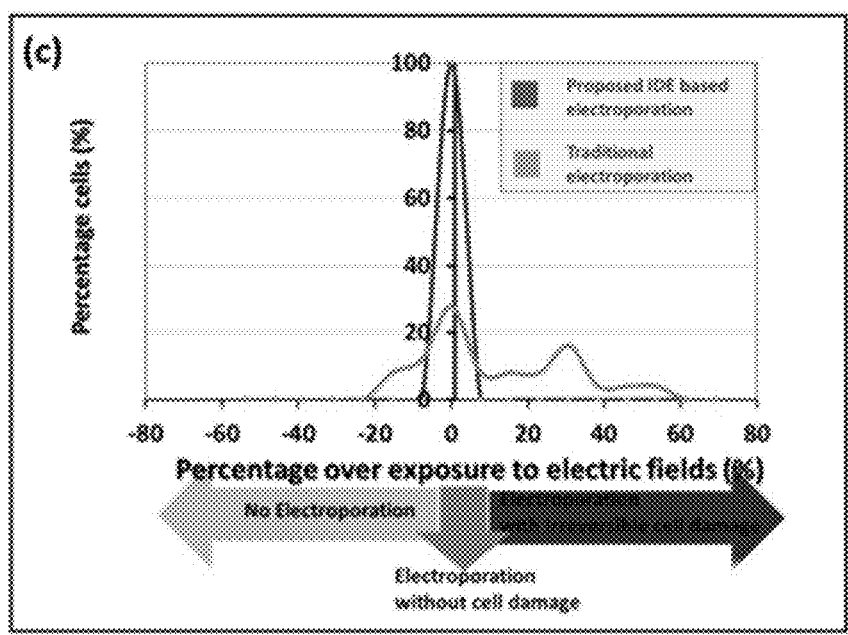

FIGS. 12A-C shows quantitative injection of mRNA molecules using electroporation. (A) Time dependent mRNA transport into T-cells. Scale bars indicate 5 μm. (B) correlation between electroporation time and number of mRNA transport into single T-cell. (C) comparison of proposed electroporation and traditional electroporation.

FIGS. 13A-G show a design of an interdigitated electrode array for effective single-file T-cell patterning for two-step electroporation. (A) Calculated electric field gradients produced by low electric potentials. (B) Fluorescence images of cell patterns produced by the electrodes of FIG. 13C. (C) Calculated electric field gradients produced by high electric potentials. (D) Fluorescence images of cell patterns produced by the electrodes of FIG. 13A. (E) Calculated electric field gradient for properly designed electrode width and spacing between electrodes as well as correct electric potential values, producing only one single-file cell pattern between each electrode pair. (F) Fluorescence image of suitable cell patterns for two-step electroporation using the device of FIG. 13E. (G) Photo of patterned single-file primary T-cells using interdigitated electrodes of FIG. 13E having proper electrode dimensions and electric potential values. Scale bars are 5 μm in FIGS. 13A, C, and E, 10 μm in FIGS. 13B, D, and F, and 20 μm in FIG. 13G. Cells were stained with calcein for easy visualization.

FIGS. 14A-E show calculated induced membrane potential values of patterned versus randomly placed T-cells on IDE, with the diameter of each T-cell being 7 μm. The external electric potential was applied between IDE and the figure shows only a section of the IDE. (A) Isometric view showing the locations of cells with respect to electrodes for randomly placed cells and their induced membrane potential values. The lower portion of the figure shows a two-dimensional view of the calculated induced membrane potential values in FIG. 14A. (B) Calculated induced potential values of patterned T-cells between electrodes, with the T-cells aligned linearly. (C) Calculated induced potential values of patterned T-cells between electrodes, with the T-cells patterned linearly but in a slightly misaligned orientation. The lower portion of the figures shows a two-dimensional view of the calculated induced membrane potential values in FIGS. 14B and C. (D) Numerical values of calculated induced membrane potential values of patterned versus randomly placed T-cells, compared also to cells placed on traditional cuvettes. The cuvette data was included to represent traditional macroelectrode-based electroporation devices. (E) Calculated induced electric potential values of cells placed in micro- and macro-electrodes. Arrows indicate the direction of the electric field. The legend shows the conversion to numerical values for FIGS. 14A, B, C, and E.

FIGS. 15A-D show a device for T-cell transfection and steps for CAR T-cell manufacturing using two-step electroporation according to the present disclosure. (A) Photo of a device for electroporation according to the present disclosure. In addition to IDE, an epoxy enclosure with open top was provided to avoid cell sample spill beyond the electrodes and no infusion pumps were provided. (B) Propidium iodide (PI) and calcein were used to demonstrate T-cell transfection, with the Figure showing fluorescence of patterned cells before electroporation. (C) Fluorescence imagery of cells after electroporation with PI. The broken-line rectangle shows a single line of patterned T-cells. (D) Calcein-staining of cells for evaluation of viability after electroporation with PI. Yellow cells indicate staining with both PI and calcein. The broken-line rectangle shows a single line of patterned T-cells. Scale bars indicate 40 μm.

Figure 16A:
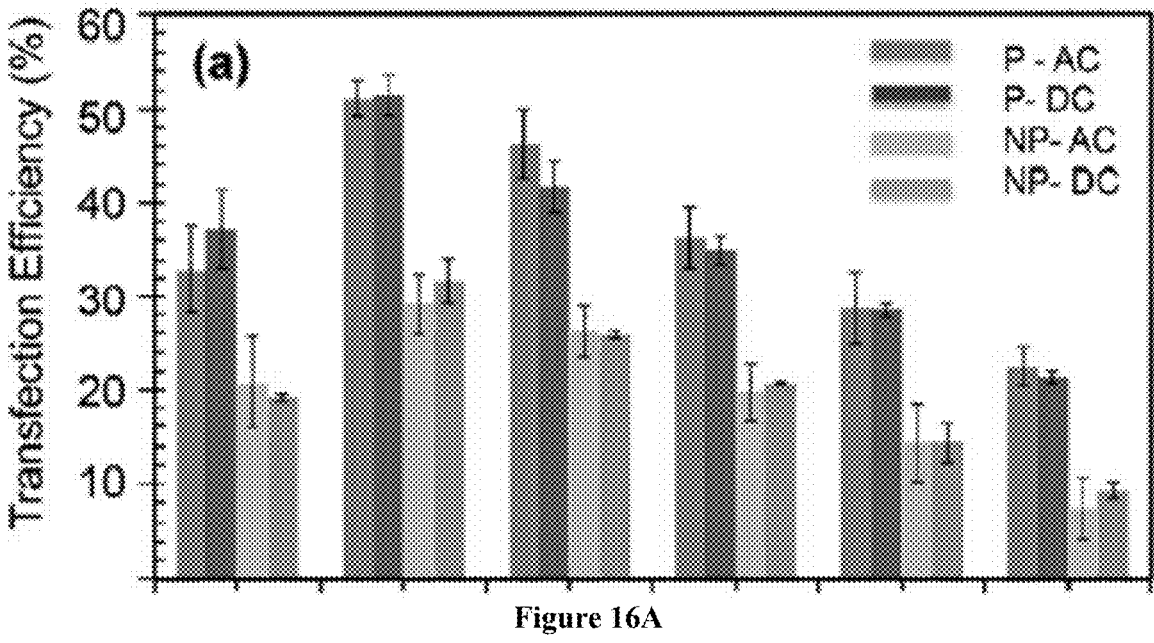
Figure 16B:
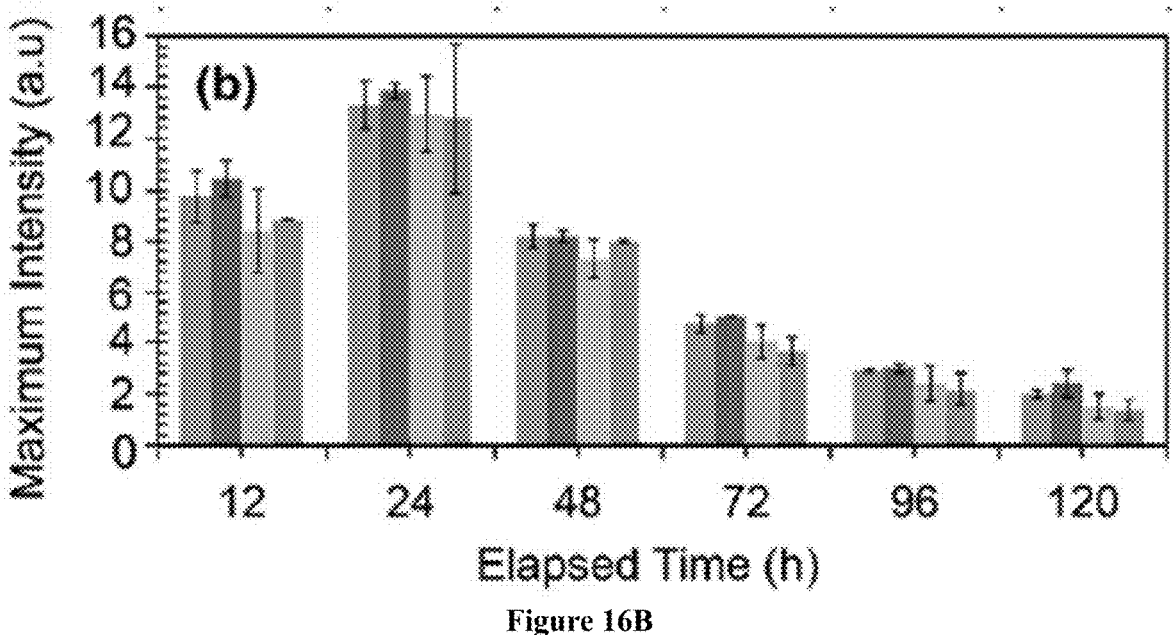

FIGS. 16A-B show transfection of T-cells electroporated as described above using enhanced green fluorescence protein (EGFP) mRNA molecules and subsequent EGFP expression. (A) Variation of transfection efficiency (number of cells expressing detectable EGFP) with time for patterned cells (P) electroporated with AC (P-AC) and DC (P-DC) electric fields versus randomly placed cells (NP) electroporated with AC (NP-AC) and DC (NP-DC) electric fields. (B) Variation of maximum fluorescence intensity with time for electroporated cells with AC and DC currents. Each electroporation experiment was repeated for patterned and randomly placed T-cells.

Figure 17A:
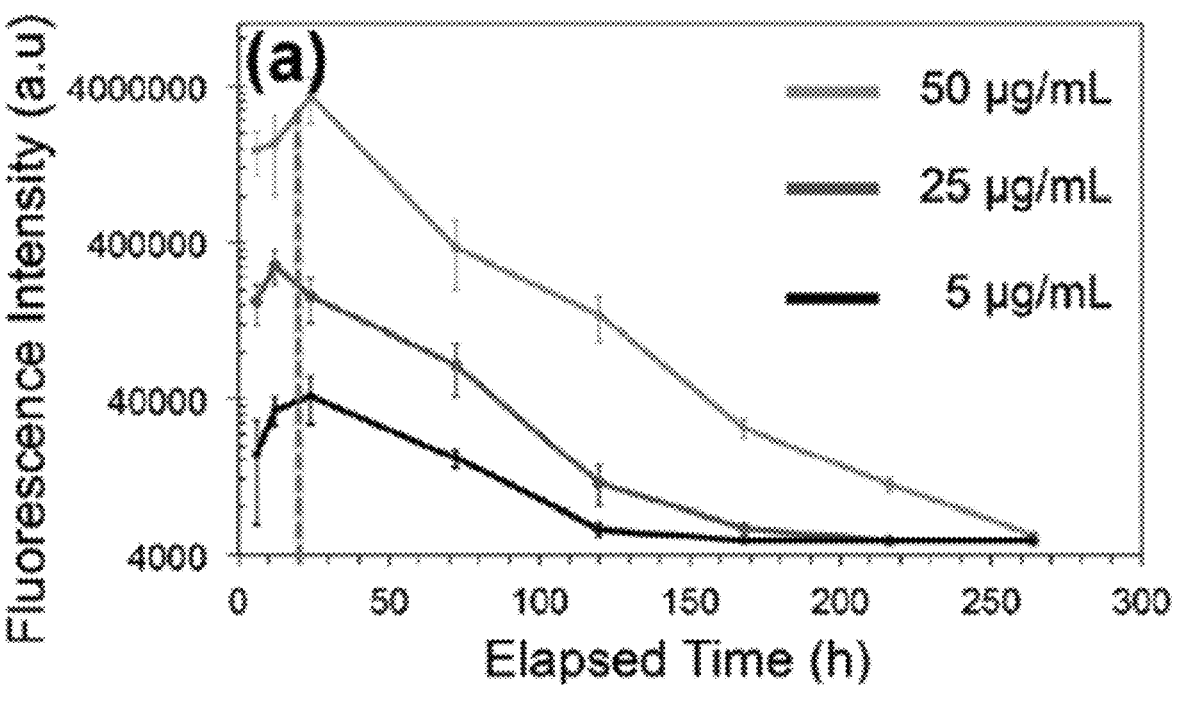
Figure 17B:
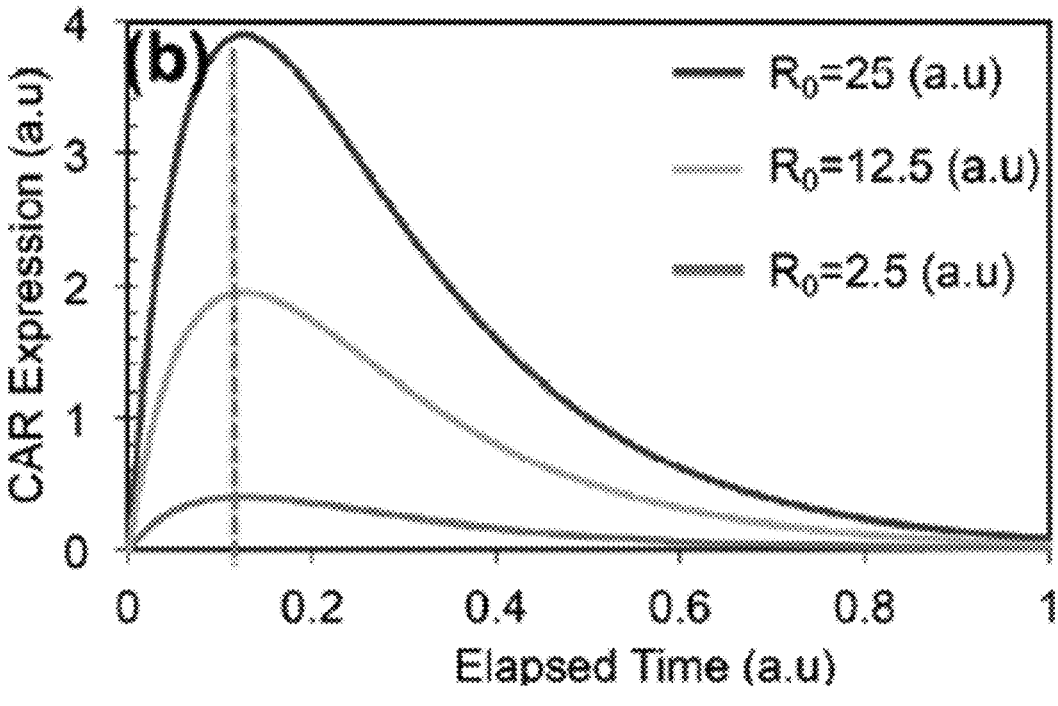

FIGS. 17A-B show variation of CAR (targeting CD19 antigen) with time for T-cells that are patterned and transfected (AC electric field) with mRNA. (A) Experimentally measured temporal variation of CAR with different mRNA concentrations in the buffer. (B) Calculated CAR expression variation with time. Calculation was performed using the expression for CAR expression obtained by solving equations derived for the compartmental model of a T-cell cytoplasm.

Figure 18:
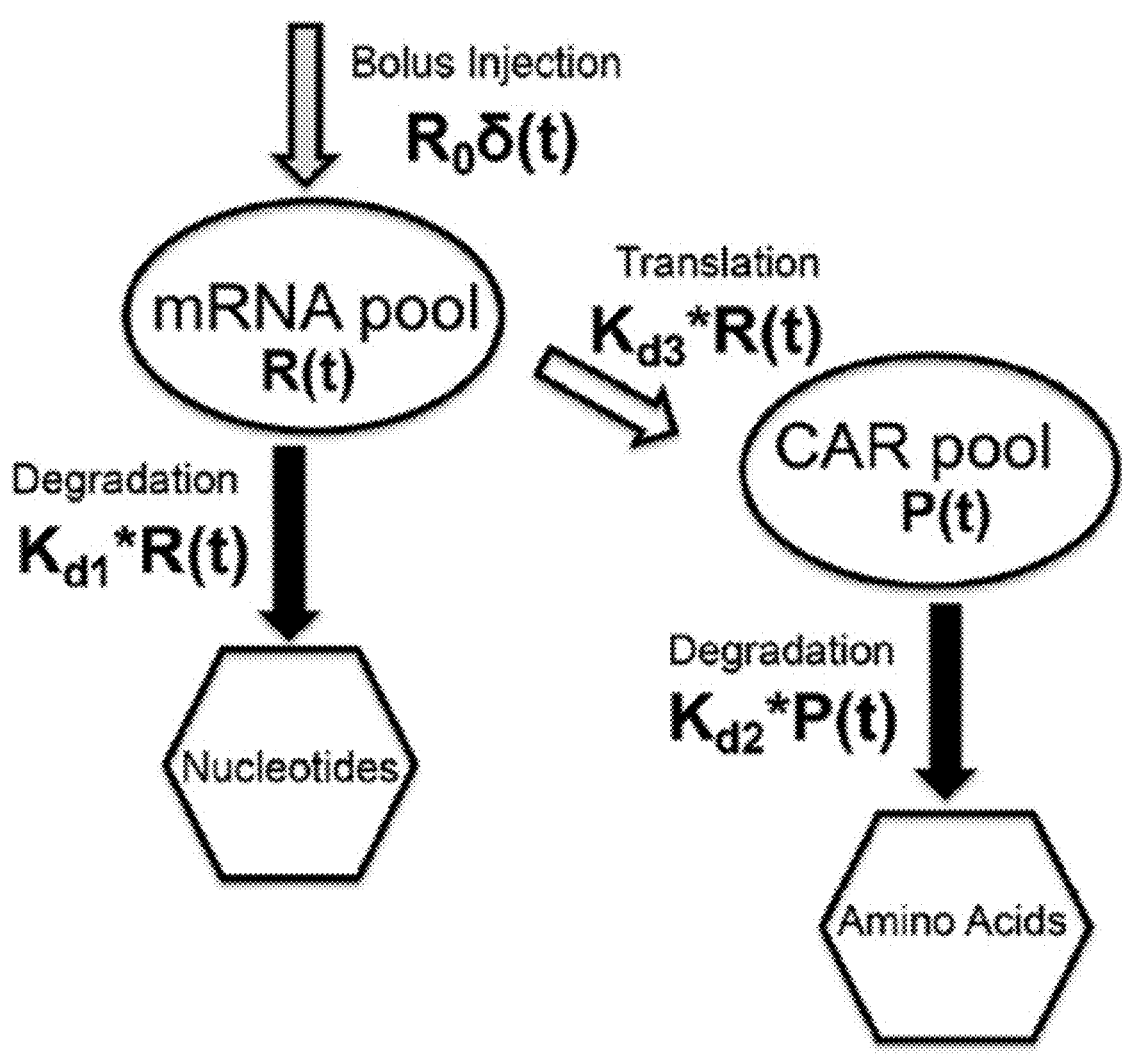

FIG. 18 illustrates the compartmental model of the T-cell cytoplasm developed to study expected CAR expression. Transfection of mRNA was assumed as bolus input to the compartmental model. Basic equations were derived using time dependent mRNA degradation and translation as well as temporal variation of CAR degradation.

Figures 19A, 19B:
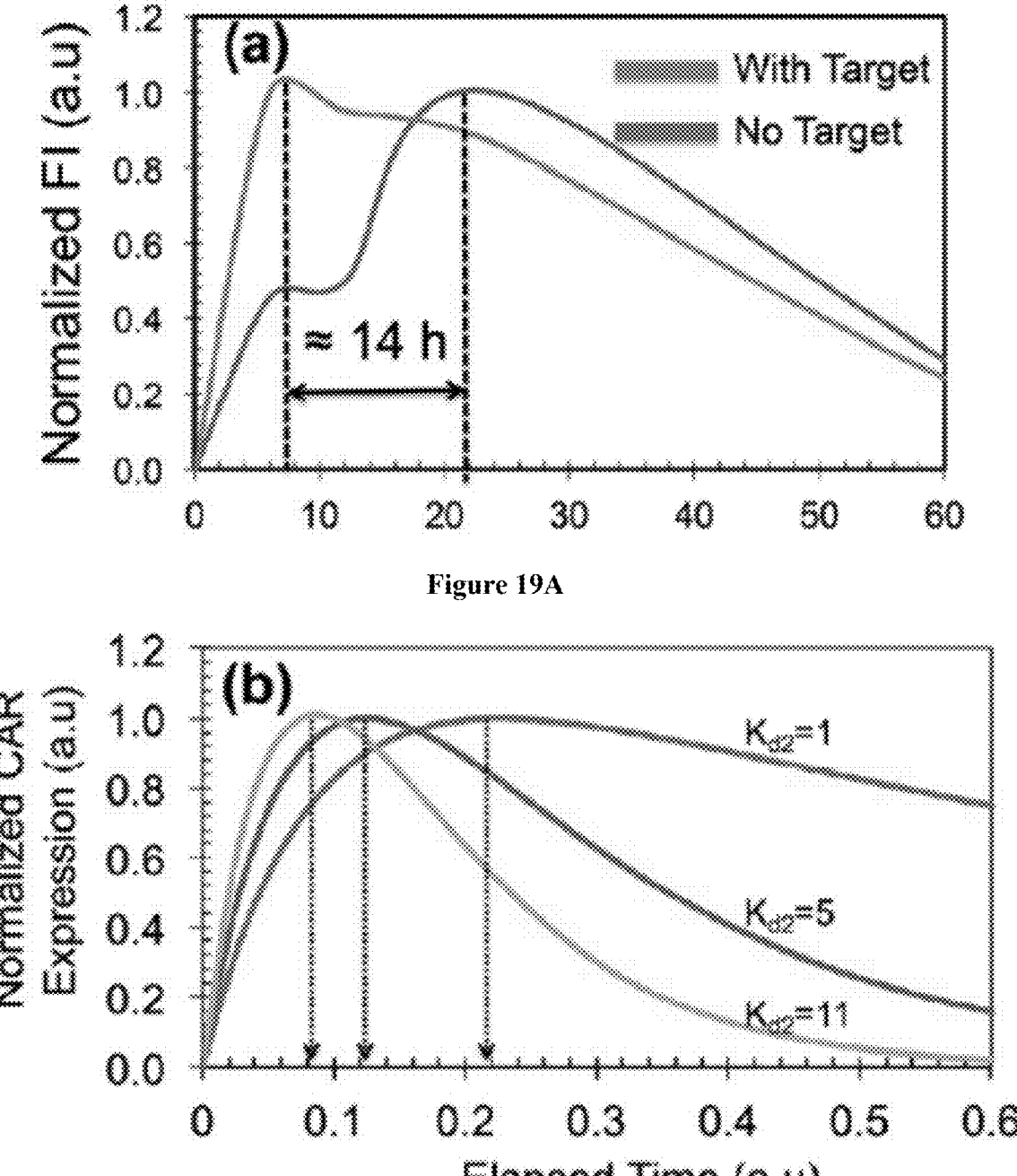

FIGS. 19A-B show temporal variation of CAR (targeting CD19 antigen) expression with and without target antigen molecules. Commercially available SUP-B15 cells expressing CD19 antigen on their cell surfaces were used. Transfection (AC electric fields) of T-cells with mRNA (50 μg mL$^{-1}$) was performed after cell patterning. CAR expression was normalized to peak values for comparison. (A) Experimentally measured CAR expression with time. (B) Calculated variation of CAR with time for $k_{d2}$ values.

Figure 20:
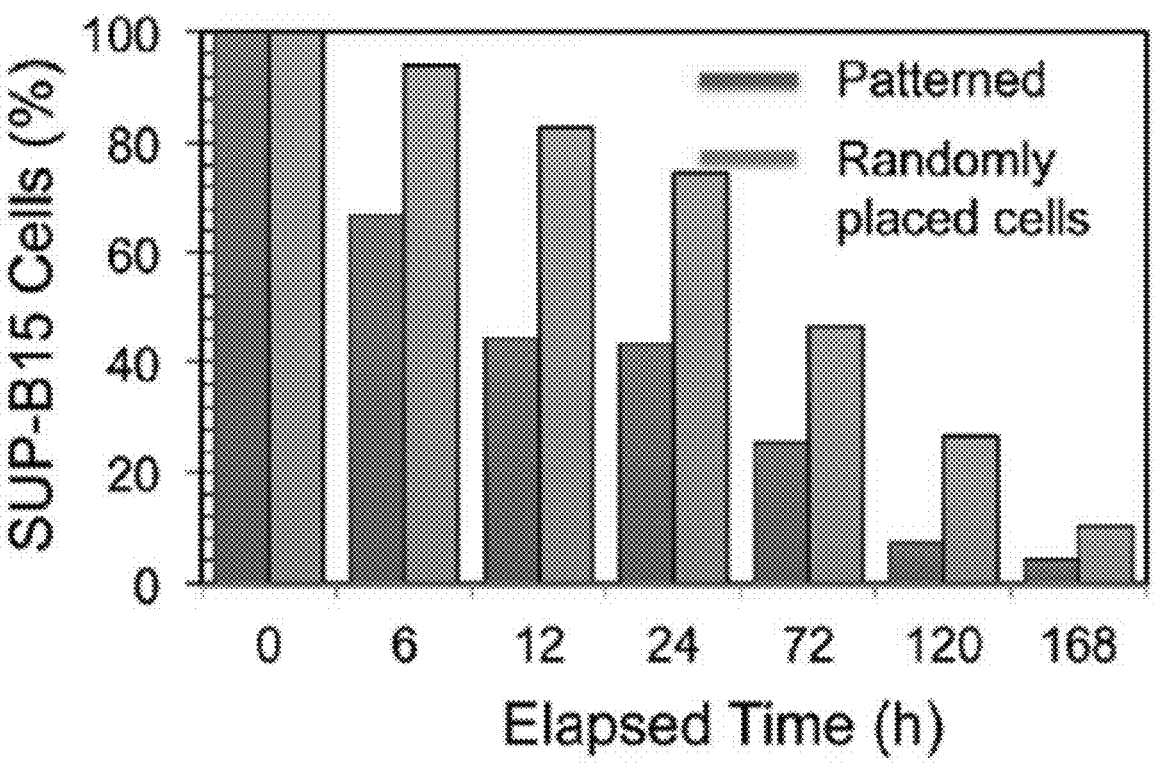

FIG. 20 shows variation of SUP-B15 cell number when co-cultured with CAR T-cells that recognize the CD 19 antigen on those cells. CAR T-cells were electroporated (AC electric fields) using 50 μg mL$^{-1}$ mRNA in the electroporation buffer and co-cultured with SUP-B15 cells beginning at t=0. Cell samples were electroporated after producing single file T-cell patterns or randomly placing T-cells in electrodes. Initially (t=0), percentage target cells were set to 100% for comparison of percentage changes with time.

Figure 21:
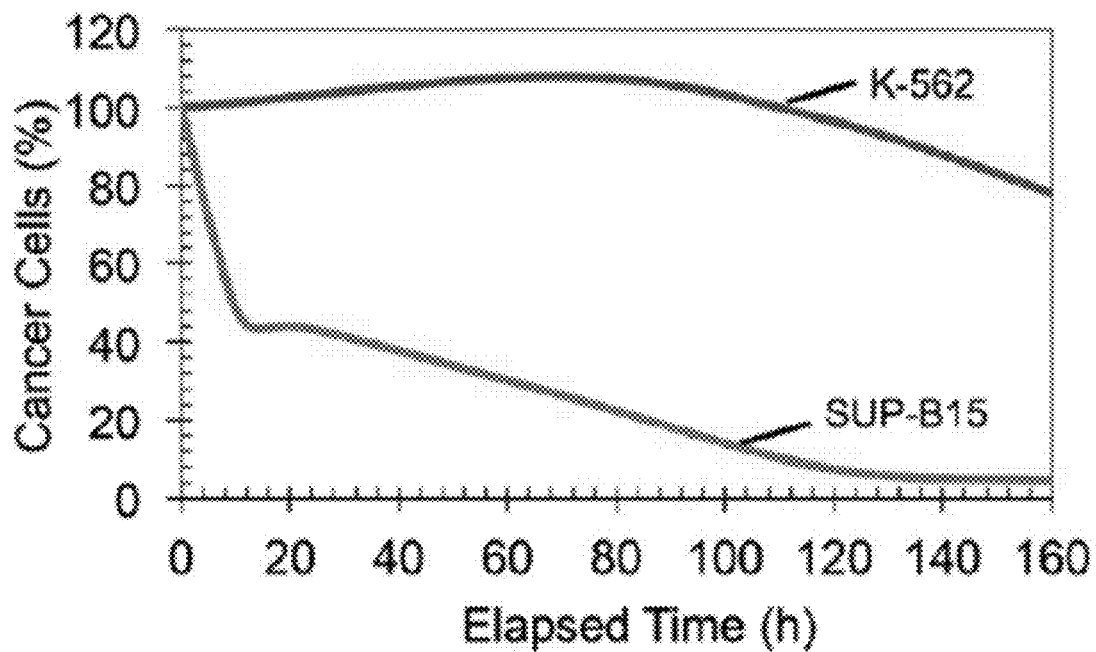

FIG. 21 demonstrates selective cancer cell killing by CAR T-cells made according to the present disclosure. CAR T-cells were manufactured by producing cell patterns and electroporated (AC electric fields) using 50 μg mL$^{-1}$ mRNA in the electroporation buffer to provide CAR T-cells targeting CD 19 antigen. The CAR T-cells were co-cultured with SUP-B15 cells (express CD 19 antigen) or K-562 cells (do not express CD 19 antigen) and co-cultured beginning at t=0.

DETAILED DESCRIPTION OF THE INVENTION

As used herein, the terms "first chamber," "chamber 1," and "region 1" may all be used interchangeably.

As used herein, the terms "second chamber," "chamber 2," and "region 2" may all be used interchangeably.

The term "DEP," as used herein, means dielectrophoresis or the migration of particles toward the position of maximum field strength or electric field gradient in a nonuniform electric field.

The term "IDE," as used herein, means micro-interdigitated electrodes.

As used herein, the terms "protein," "protein ligand," and "ligand" may all be used interchangeably.

The term "PDMS," as used herein, means polydimethylsiloxane.

The term "rms," as used herein, means root mean square.

The presently-disclosed subject matter relates to a new device for a scalable, biomanufacturing platform for the production of CAR-modified T-cells while eliminating on-target/off-tumor toxicity and decreasing the current production cost by 500 times (per treatment). In some embodiments, the presently-disclosed subject matter includes a device to produce modified T-cells comprising a first chamber for proliferating a population of T-cells and a second chamber for modifying the T-cells to express a desired T-cell receptor antigen.

Figure 2:
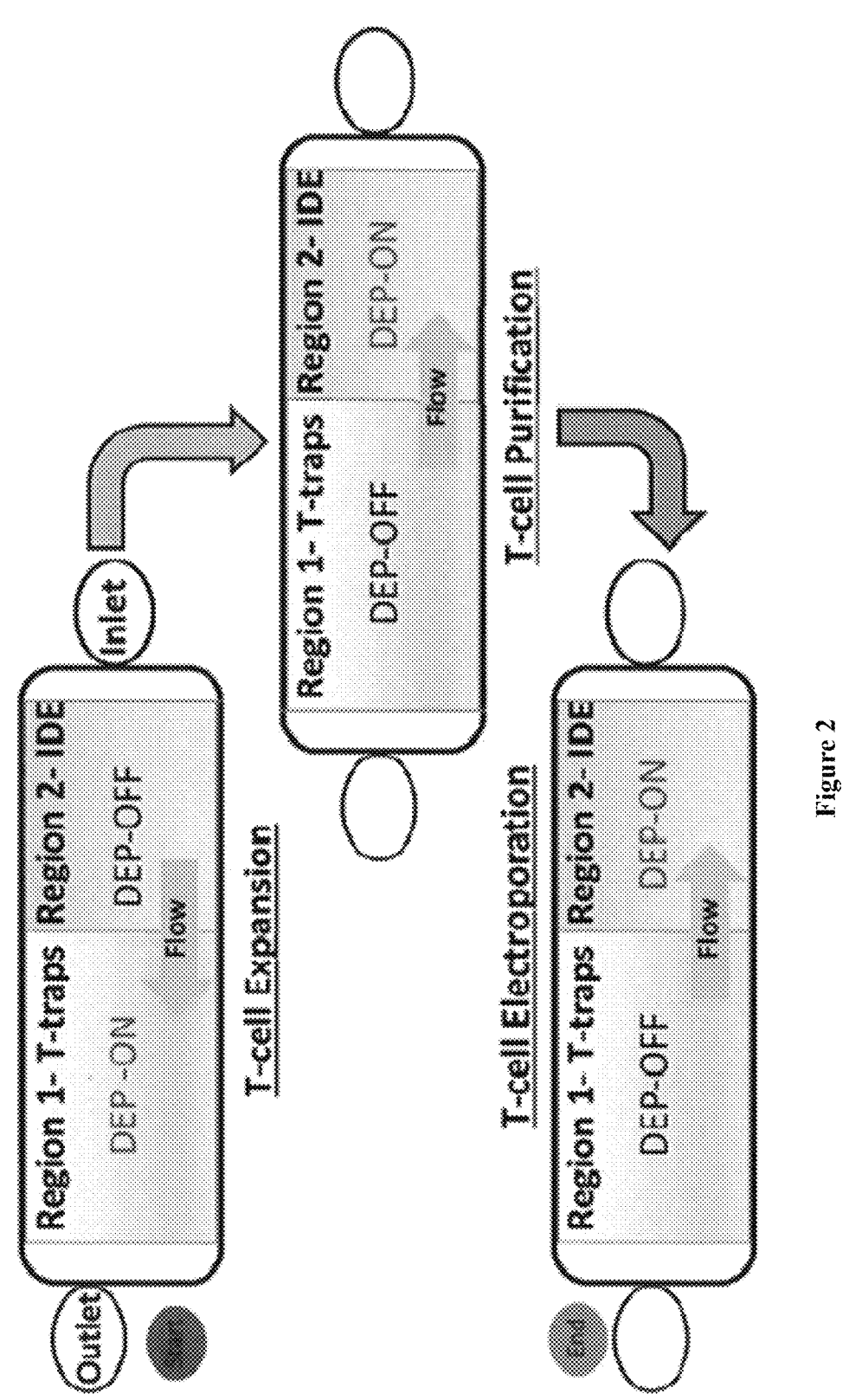
FIG. 2 shows the basic steps of the present invention for manufacturing T-cells with CAR receptors.
Figure 3:
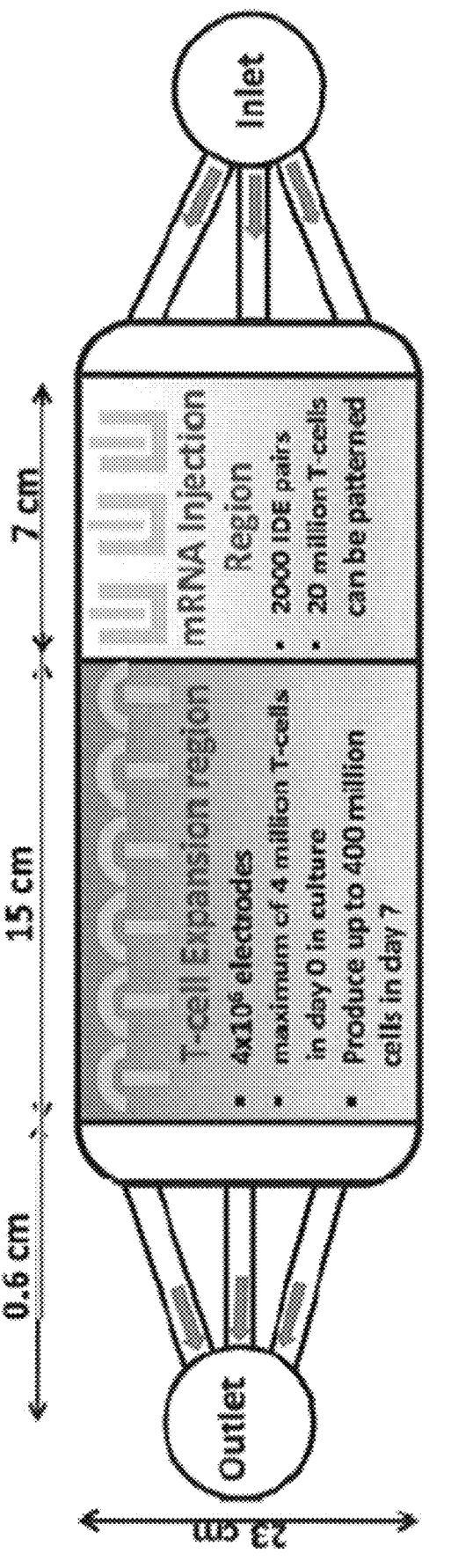
FIG. 3 shows Schematic representation of the scaled-up, integrated CAR T-cell manufacturing device to produce $10^7$ CAR T-cells.

In some embodiments, the device includes a first chamber and a second chamber. Each of chamber 1 and chamber 2 comprises two parallel surfaces and four sides. Two of the sides are parallel to each other and are the side sides. The other two sides are somewhat parallel to each other and are the ends. One or more of the two end sides may be curved or beveled to improve the efficiency of the flow in and out of the chambers. The parallel surfaces are the top and bottom of the chambers and are usually rectangular-like in shape, except one or more of the edges of the top and bottom surfaces may be curved or beveled to match one or more of the curved or beveled sides. The top and bottom are separated from each other by a distance of from about 30 μm to about 1000 μm, preferably by a distance of from about 30 μm to about 400 μm, more preferably by a distance of from about 30 μm to about 200 μm, most preferably by a distance of about 100 μm. The two end sides of each chamber that are parallel to each other may have openings or ports to allow T-cells to flow into and out of the chambers. The top and sides of the chamber 1 can be any suitable material, including, but not limited to, glass, PDMS, or a combination thereof. For example, in one embodiment, the bottom material is glass and the top and side material is PDMS. In a preferred embodiment of the invention, one end side of chamber 1 and one end side of chamber 2, usually end sides that are not curved or beveled, can abut each other so that the two chambers are one integrated unit sharing one end of each chamber. FIG. 2 and FIG. 3 illustrate the top view of a preferred integrated device chamber comprising both chamber 1 and chamber 2.

The dimensions of chamber 1 can be from about 10 cm to about 50 cm end to end, preferably from about 10 cm to about 30 cm end to end, more preferably from about 10 cm to about 20 cm end to end. The dimensions of chamber 1 can be from about 10 cm to about 75 cm side to side, preferably from about 10 cm to about 50 cm side to side, more preferably from about 20 cm to about 30 cm side to side.

In one embodiment, chamber 1 is about 15 cm long on its side sides, about 23 cm wide on its end sides, and about 100 μm deep for the width of the sides and ends. In another embodiment, chamber 2 is about 7 cm long on its side sides, about 23 cm wide on its end sides, and about 100 μm deep for the width of the sides and ends.

A suitable population of T-cells to be proliferated in the first chamber (also known as chamber 1) can be obtained from a blood sample. The blood sample can be any matching blood sample but preferably is obtained from the patient to be treated with the CAR modified T-cells. Purification and isolation of T-cells from the blood sample can be accomplished by known methods. The T-cell population is suspended in a suitable buffer for insertion into chamber 1. The starting T-cell population is from about 1 million cells to about 50 million cells, preferably from about 5 million cells to about 25 million cells, most preferably about 10 million cells. Typically, 5 ml of human blood contains about 2.5-9.0 million T-cells.

The role of chamber 1 is to expand or proliferate a population of T-cells to significantly increase their number. A significant increase is from about 100 fold to a maximum of about 1000 fold. This is accomplished by trapping small subpopulations of the T-cells to increase their density. With a higher density of T-cells in a localized area, they can be subjected to known reagents and cytokines to increase their number. Trapping the T-cells occurs using cell traps, micro-traps or T-traps that have a particular geometrical shape, and also applying an electric field to the cells in a T-trap. The T-traps are individually a localized structure, but they do have access to the entire area of chamber 1 so that cells can flow into and out of the T-traps under appropriate conditions.

In some embodiments, the T-traps are fabricated to be within the enclosed chamber 1. In one embodiment, each trap includes a capture container and a guiding container. In another embodiment, each container is constructed of an electrical conducting material and attached to an electric potential source. In some embodiments, the containers are constructed of a metal material such as gold (Au), silver (Ag), platinum (Pt), copper (Cu), iron (Fe), aluminum (Al), Tin (Sn), Nickel (Ni), Carbon (C), doped silicon (Si) or an alloy of metals. Preferred electrical conducting materials are Au, Ag, Pt and indium tin oxide. The capture container can be a flat surface or a concave surface with the opening of the concave surface facing the guiding container. FIGS. 3, 4A-C, and 5A-C show preferred configurations of the two containers. In this way, the starting population of T-cells can be electrically guided to the capture container to increase a localized subpopulation of T-cells for expansion. As long as the electric potential is maintained the T-cell population stays concentrated at or near the capture container. The electric potential that is used to guide the T-cells is from about 10 milli Volts peak to peak (mVpp) to about 200 mVpp, preferably at about 100 mVpp.

To allow for expansion of the T-cell population, the open, unoccupied volume of chamber 1 should be sufficient to allow at least 100 million, preferably at least 500 million, and more preferably at least a billion T-cells after expansion takes place. T-cells typically have a diameter of about 20-40 μm. To encourage growth, the media in which the T-cells are captured can contain reagents selected from the group consisting of nutrients, food and cytokines. During the preferred 1000 fold expansion, components to produce cellular structure, energy production and growth will shorten the time for the expansion to take place. The appropriate nutrients, food and cytokines for a particular population of T-cells is known to those of skill in the art as is the temperature and other growth conditions. Growth and expansion of the T-cell population can be monitored by standard techniques such as spectrophotometry and standard curves.

Once the T-cell population in chamber 1 reach the desired expanded cell population amount and/or density, the electrical field can be turned off so the T-cell population in chamber 1 can be moved to chamber 2 by physically flushing the cells or using a syringe pump. In certain embodiments, where chamber 1 and chamber 2 abut each other, inserting a syringe into an opening of the side opposite the side of chamber 1 that abuts chamber 2 will allow the T-cells to be flushed through and opening in the shared side between chamber 1 and chamber 2.

Figures 6A, 6B, 6C:
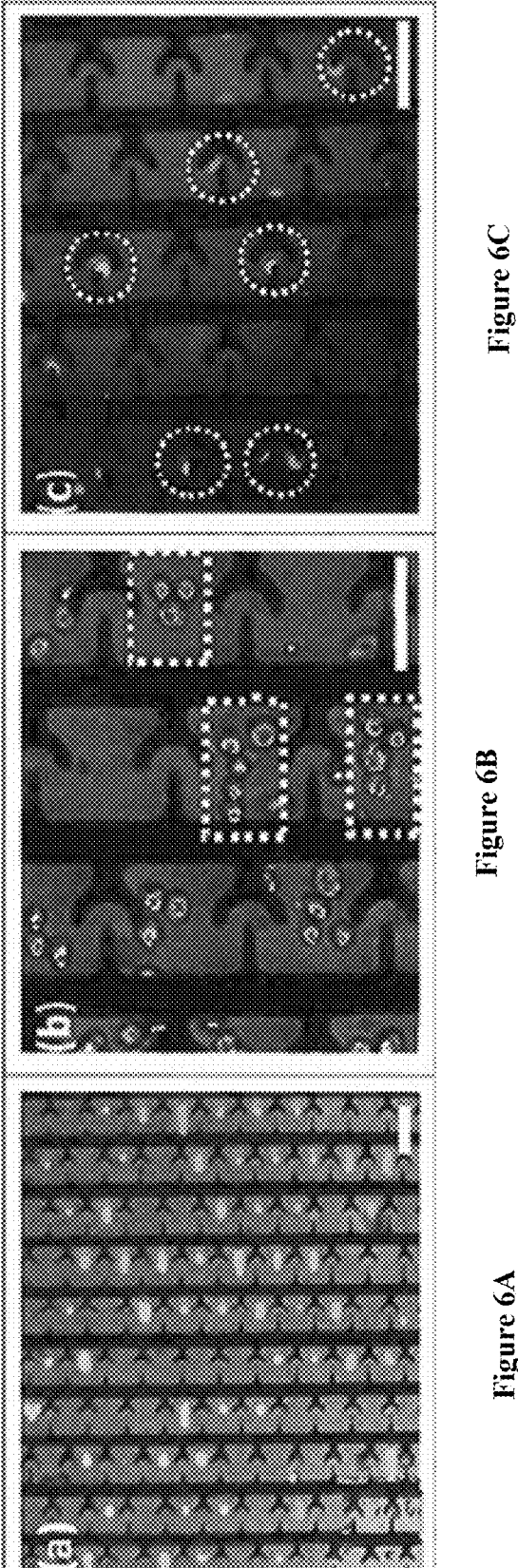
FIGS. 6A-C show cells and beads trapped using DEP force. (A) Combined bright field and fluorescent image of the electrodes and trapped fluorescent beads (diameter=10 micrometers) using negative DEP. Note that clusters of beads are trapped. (B) Bright field view of trapped myoblast cells (C2C12) using negative DEP (white rectangles with broken lines). Clusters of cells were trapped near the electrodes. (C) Fluorescent image of the trapped C2C12 cells using positive DEP. Note that single C2C12 cells (white circles with broken lines) are trapped on the electrodes. Scale bars indicate 100 micrometers.

In some embodiments, during T-cell expansion, negative DEP is used to form T-cell clusters as indicated in FIG. 6B and initiate T-cell expansion. This facilitates close monitoring of the T-cell expansion rate. Alternatively, if there is not acceptable expansion (~100×), positive DEP (with single T-cells) may be used to expand the T-cells. If positive DEP is effectively expanding T-cells, static conditions may be used to expand T-cells. Briefly, T-cells are trapped using −ve or +DEP and turn off the traps and culture cells with beads. Negative DEP is a repulsion force on T-cells from the electrodes. In negative DEP, T-cells will move away from the electrode and go to the weakest electric field area. The positive DEP is the exactly the opposite of the negative DEP. In one embodiment, the T-cell expansion is about 100×. In another embodiment, increasing T-cell expansion includes increasing the number of T-traps and/or increasing the number of T-cells in day 0. In a further embodiment, if there is not rapid expansion within 10 days, a flow of a mixture of Interleukin-2 (IL-2, $10^3$ IU/mL), anti-CD3 (0.1 μg/mL) and anti-CD28 (0.25 μg/mL) may be applied. Without wishing to be bound by theory, it is believed that this mixture will efficiently expand T-cells.

The role of chamber 2 is to modify the T-cells in the expanded T-cell population so that they will present on their surface membrane a protein, protein ligand or ligand, which will bind to one or more cell surface proteins on a targeted cancer cells. In one embodiment, the protein ligand is chimeric in that besides a region that will bind to one or more cell surface proteins on targeted cells, such as cancer cells, it also has a region that that includes hydrophobic amino acids so that it will bind to the T-cell membrane through hydrophobic bonding. As a result, in another embodiment, the protein ligand is presented outside the T-cell and is available to bind cell surface proteins on the targeted cells. In a further embodiment, this brings the T-cell in contact with the targeted cells, permitting the T-cell to perform the role of a T-cell and kill targeted cancer cells. In this way, the modified T-cells will bind specifically to the targeted cells.

Once the T-cells bind, they can perform the role of a T-cell and kill the targeted cell, such as a cancer cell. The most effective way to do this is to insert genetic material into most, if not all, the T-cells of the expanded T-cell population so the T-cells will express the protein coded by the mRNA. A number of such mRNA molecules are known that code for such chimeric antigen receptor (CAR) proteins that bind to various cancer cells. However, the device of the present invention allows a more homogenous insertion of the mRNA into the T-cells in a much shorter time and at a much lower cost. By homogenous insertion, it is meant each T-cells received a similar number of mRNA molecules and most, if not all, T-cells receive that number of mRNA molecules. A preferred amount of mRNA used per T-cell sample, after expansion (up to about a billion T-cells) is from about 100 μg/mL to about 1000 μg/mL, preferably about 100 μg to about 700 μg/mL, more preferably about 200 μg/mL to about 500 μg/mL. The mRNA is preferably in a homogenous distribution in the solution in chamber 2 before, during and after the patterning of the T-cells occurs.

The magnitude of induced electric potential (electric field) in T-cell membranes determines the size of the pore that is used to transport exogenous mRNA molecules through electroporation. Therefore, in some embodiments, producing a homogenous mixture of T-cells transfected with mRNA molecules includes inducing a uniform electric field in all T-cell membranes in the cell mixture. In one embodiment, inducing a uniform electric field includes patterning T-cells in single files in a channel between parallel micro-electrodes so that every single T-cell will be subjected to the same external electric field. In another embodiment, the micro-electrodes include micro-interdigitated electrodes (IDE). Lithography based microfabrication can be used to fabricate the IDE in chamber 2 of the present invention using any of the electrical conducting materials used in chamber 1 on glass substrates. The space between electrodes can be anywhere from about the diameter of typical T-cells to about twice the diameter of typical T-cells, or preferably about 30 μm to accommodate a single file of T-cells between electrodes.

With one or more channels for T-cell patterning constructed in chamber 2, T-cell patterning is achieved through the use of DEP. The DEP patterning of the T-cells can use an AC electric potential of from about 20 mV to about 500 mV, preferably from about 60 mV to about 200 mv, most preferably at about 100 mV. FIG. 11A illustrates the IDEs of one preferred embodiment designed and fabricated for cell patterning/electroporation experiments. Under these electric field conditions, more than 99% of the T-cells that were on the electrodes can be patterned. Finally, we turned off the electric field (DEP) and observed that patterned T-cells do not move or become disturbed.

The dimensions of chamber 2 can be from about 4 cm to about 25 cm end to end, preferably from about 5 cm to about 20 cm end to end, more preferably from about 5 cm to about 10 cm end to end. In one embodiment, for example, the dimensions of chamber 2 is about 7 cm long on its side sides, about 23 cm wide on its end sides and about 100 μm deep for the width of the sides and ends. The dimensions of chamber 1 can be from about 10 cm to about 75 cm side to side, preferably from about 10 cm to about 50 cm side to side, more preferably from about 20 cm to about 30 cm side to side.

Once the T-cells are patterned into a single file, electroporation can be performed. This is achieved by applying a DC current pulse (DCP) of a suitable strength and for a suitable time across the electrodes lining each side of the T-cell patterning channel. For example, in some embodiments, A DCP of suitable strength and duration to electroporate T-cells includes any DCP that provides about $1.25 \times 10^5$ V/m induced electric field in the T-cell membrane. Suitable DCP current strength can be from about $0.1 \times 10^5$ V per pulse (V/P) to about $10 \times 10^5$ V/P, preferably from about $0.5 \times 10^5$ V/P to about $4 \times 10^5$ V/P, most preferably about 1.5V/P. The DCP current can have a pulse (P) length for a period of time from about 0.1 ms (milli seconds) to about 50 ms, preferably from about 1 ms to about 10 ms, post preferably about 5 ms. Electroporation equipment is commercially available. In alternative embodiments, as shown in the Figures and discussed herein, AC electroporation is contemplated and suitable.

Following electroporation, the T-cells can be removed from chamber 2, suspended in an appropriate buffer and the T-cells purified from other components in chamber 2 such as medium, proteins, nutrients, cytokines, etc. and then stored for up to about 10 days before further formulation and administration to a patient in need thereof. In some embodiments, for example, the device disclosed herein produces modified T-cells for treating cancer. The modified T-cell population may be formulated and administered to a patient as determined by the attending physician. Administration of the T-cells includes any suitable methods, such as, but not limited to, injection or infusion over a period of time. The device produces sufficient modified T-cells for at least a single administration, although more than one cycle of administration may be called for depending on the stage of the cancer, age, and health of the patient and the like.

Accordingly, the instant disclosure provides a device that is inexpensive, rapid, easy to manufacture, easy to use, efficient, effective, and capable of producing CAR T-cells for administration to patients where the patient is located. In addition, as compared to existing devices and methods, the device disclosed herein provides markedly improved CAR modified T-cell production while reducing or eliminating the toxicity and high production cost. By overcoming on-target/off-tumor toxicity and high production costs, the presently-disclosed subject matter provides an innovative solution that permits widespread adoption and may be the most transformative development in cancer therapy since the discovery of chemotherapeutics.

Although discussed above with regard cancer patients and cancer therapy, as will be appreciated by those skilled in the art, the instant disclosure is not so limited. Other disease to which the instant disclosure is applicable include, but are not limited to, infections, heart diseases, and stem cell therapy, all of which are expressly contemplated herein.

In addition, although discussed above with regard to T-cells, as will be understood by those skilled in the art, the presently-disclosed subject matter it not so limited and may include any other field or type of cell where electroporation is desired. For example, in one embodiment, the device disclosed herein may be used for stem cell research and/or stem cell electroporation. In another embodiment, the presently-disclosed subject matter reduces or eliminates the lysing of stem cells as compared to existing electroporation techniques, where 99% of stem cells are lysed during the transfection of genes/proteins.

Also provided herein is a kit including the device according to one or more of the embodiments disclosed herein combined with compatible accessories to make use of the device easier. Such accessories can include one or more items selected from the group consisting of syringes, nutrients, food, cytokines, buffers, storage containers, transfer vehicles and the like. The kit can also include instructions for optimal use of the device.

The details of one or more embodiments of the presently-disclosed subject matter are set forth in this document. Modifications to embodiments described in this document, and other embodiments, will be evident to those of ordinary skill in the art after a study of the information provided in this document. The information provided in this document, and particularly the specific details of the described exemplary embodiments, is provided primarily for clearness of understanding and no unnecessary limitations are to be understood therefrom. In case of conflict, the specification of this document, including definitions, will control.

When the term "including" or 'including, but not limited to" is used, there may be other non-enumerated members of a list that would be suitable for the making, using or sale of any embodiment of this invention.

While the terms used herein are believed to be well understood by those of ordinary skill in the art, certain definitions are set forth to facilitate explanation of the presently-disclosed subject matter.

Unless defined otherwise, all technical and scientific terms used herein have the same meaning as is commonly understood by one of skill in the art to which the invention(s) belong.

All patents, patent applications, published applications and publications, GenBank sequences, databases, websites and other published materials referred to throughout the entire disclosure herein, unless noted otherwise, are incorporated by reference in their entirety.

Although any methods, devices, and materials similar or equivalent to those described herein can be used in the practice or testing of the presently-disclosed subject matter, representative methods, devices, and materials are described herein.

The present application can "comprise" (open ended) or "consist essentially of" the components of the present invention as well as other ingredients or elements described herein. As used herein, "comprising" is open ended and means the elements recited, or their equivalent in structure or function, plus any other element or elements which are not recited. The terms "having" and "including" are also to be construed as open ended unless the context suggests otherwise.

Following long-standing patent law convention, the terms "a", "an", and "the" refer to "one or more" when used in this application, including the claims. Thus, for example, reference to "a cell" includes a plurality of such cells, and so forth.

Unless otherwise indicated, all numbers expressing quantities of ingredients, properties such as reaction conditions, and so forth used in the specification and claims are to be understood as being modified in all instances by the term "about". Accordingly, unless indicated to the contrary, the numerical parameters set forth in this specification and claims are approximations that can vary depending upon the desired properties sought to be obtained by the presently-disclosed subject matter.

As used herein, the term "about," when referring to a value or to an amount of mass, weight, time, volume, concentration or percentage is meant to encompass variations of in some embodiments ±20%, in some embodiments ±10%, in some embodiments ±5%, in some embodiments ±1%, in some embodiments ±0.5%, and in some embodiments ±0.1% from the specified amount, as such variations are appropriate to perform the disclosed method.

As used herein, ranges can be expressed as from "about" one particular value, and/or to "about" another particular value. It is also understood that there are a number of values disclosed herein, and that each value is also herein disclosed as "about" that particular value in addition to the value itself. For example, if the value "10" is disclosed, then "about 10"

is also disclosed. It is also understood that each unit between two particular units are also disclosed. For example, if 10 and 15 are disclosed, then 11, 12, 13, and 14 are also disclosed.

As used herein, "optional" or "optionally" means that the subsequently described event or circumstance does or does not occur and that the description includes instances where said event or circumstance occurs and instances where it does not. For example, an optionally variant portion means that the portion is variant or non-variant.

EXAMPLES

Example 1: Integrate Basic Steps of CAR Modified T-Cell Engineering and Demonstrate the Production of CAR Modified T-Cells (~10 Million) for a Single Treatment at 500 Times Cheaper than Current Cost FIG. 2 illustrates the basic steps involved in manufacturing about 10 million T-cells expressing ErbB2 immunoreceptor molecules. Briefly, isolated T-cells are expanded in the T-trap electrode area (region 1), (T-cell expansion). In Examples 2 and 5 below, the experimental conditions needed for T-cell expansion are determined. The DEP in the T-cell expansion area is then turned off and cells are flown over IDE electrodes (region 2) when DEP is applied in the IDE area (T cell purification). T-cells are selectively patterned in the IDEs. Since beads do not experience DEP, this step purifies the T-cells by washing away beads. The experimental conditions from Example 2 are then used to trap T-cells, which is followed by flowing in the ErbB2 mRNA and electroporating T-cells (T-cell electroporation). Finally, electroporated T-cells are collected and suspended in the RPMI 1640 and incubated for the expression of immunoreceptors. Thereafter, the expression levels of ErbB2, cytotoxicity, and cytokine release during the presence of target tumor cells is analyzed. Based on the results, necessary adjustments to the design and critical experimental parameters are determined.

To integrate procedures, an IDE electrode array and a T-trap array were fabricated in a single device. These electrode arrays were fabricated in Au (gold) on a glass substrate. A simple layout of the scaled-up device is illustrated in FIG. 3. 12 inch commercially available glass wafers (University Wafer, Boston, Mass.) were used to fabricate a prototype of the device. Fabrication of electrodes included soft lithography, sputtering of 1000 Å layer of Au and traditional photoresist lift-off in Acetone. The detailed fabrication procedure is reported elsewhere.

Once the electrode manufacturing is finished, the glass wafer was diced to achieve the desired dimensions of the device. A Polydimethylsiloxane (PDMS) flow channel was then produced to flow T-cells in and out of the device. PDMS provides significantly improved temperature and gas exchange between proliferating T-cells and outside, resulting in favorable culture conditions inside the device. Briefly, a PDMS mold was manufactured to the desired dimensions using 3D printing and commercially available PDMS and was poured onto the mold and cured in an oven. After curing for 3-4 hours, PDMS channels were peeled off from the mold. Inlets and outlets were made using a commercially available hole punch. Finally, PDMS channels and Electrodes were exposed to 02 plasma and bonded to produce the device.

The lytic and activating thresholds are used to find the minimum immunoreceptor level needed to produce CAR T-cells. Once the immunoreceptor level is determined, the device expands, purifies, and electroporates T-cells, producing a number of CAR T-cells sufficient for a single treatment. The overall objective is to integrate the basic steps into a single integrated device to produce about $10^7$ T-cells. The overall outcome of this is to demonstrate the production of ErbB2 modified T-cells for a single treatment cost-effectively.

Finally, the potency of the manufactured T-cells in eliminating tumors is monitored. The instant inventors have developed an electrical impedance based label-free method that detects the dielectric properties of the cells at single-cell resolution. The T-cells must be patterned in IDE electrodes to measure the dielectric properties. The process involves measuring the bulk impedance of the cell/medium and uses Scharama's impedance model to find the dielectric properties of individual T-cells. Therefore, the technology disclosed herein qualifies as one of the cGMP manufacturing technologies.

The resulting information is then used to develop a massively parallel single-cell electroporation technique to quantitatively transfect T-cells with CAR expressing mRNA molecules and produce homogenous mixture of CAR expressing T-cells. This capability is utilized to produce the minimum number of immunoreceptors needed in T-cells to efficiently lyse tumor cells thereby minimizing the interactions with healthy tissues and eliminating on-target/off-tumor toxicity. This T-cell manufacturing procedure is scaled-up through the integration of T-cell engineering, expansion and purification to produce a large number of CAR-modified T-cells. In each step, T-cells are manipulated through the use of dielectrophoresis (DEP), the phenomenon in which a force is generated selectively on T-cells when cells are exposed to non-uniform electric fields.

Example 2: Isolation of T-Cells from Patient Blood Sample

Resting CD4$^+$ and CD8$^+$ T cells are isolated from whole human blood obtained from Bioreclamations Inc (Westbury, N.Y.) using a well-established technique. Briefly, lymphocytes are isolated using a density gradient by layering blood on top of the Ficoll-Paque followed by mononuclear removal and red blood cell lysis. Finally, resting CD4$^+$ and CD8$^+$ T cells are negatively isolated using standard Miltenyi isolation kits (Cambridge, MA). The isolated T-cells are suspended in RPMI 1640. Standard quality control procedures are implemented to check T-cells.

The same procedure can be used with patient blood.

Example 3: Expansion of T-Cell Population in Chamber 1

Figures 4A, 4B, 4C:
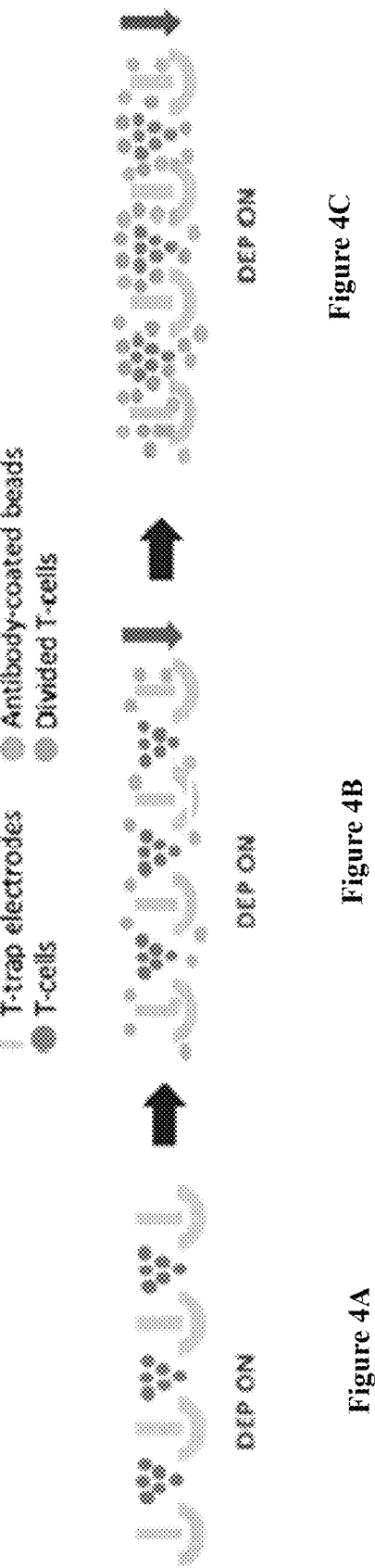
FIGS. 4A-C show schematic diagram of the proposed T-cell engineering for expansion; (A, B, C) T-cell expansion. (A) Trap T-cells using DEP, (B) Flow antibody coated beads, (C) expansion of T-cells.

As indicated in FIGS. 4A-C, during T-cell expansion, T-cells are trapped on the electrodes. FIG. 2 illustrates the basic steps of the production of CAR T-cells and FIGS. 4A-C show the steps of T-cells expansion, which involves trapping T-cells as clusters using negative DEP, flow CD3+/CD28+ beads and expansion.

Figure 5A:
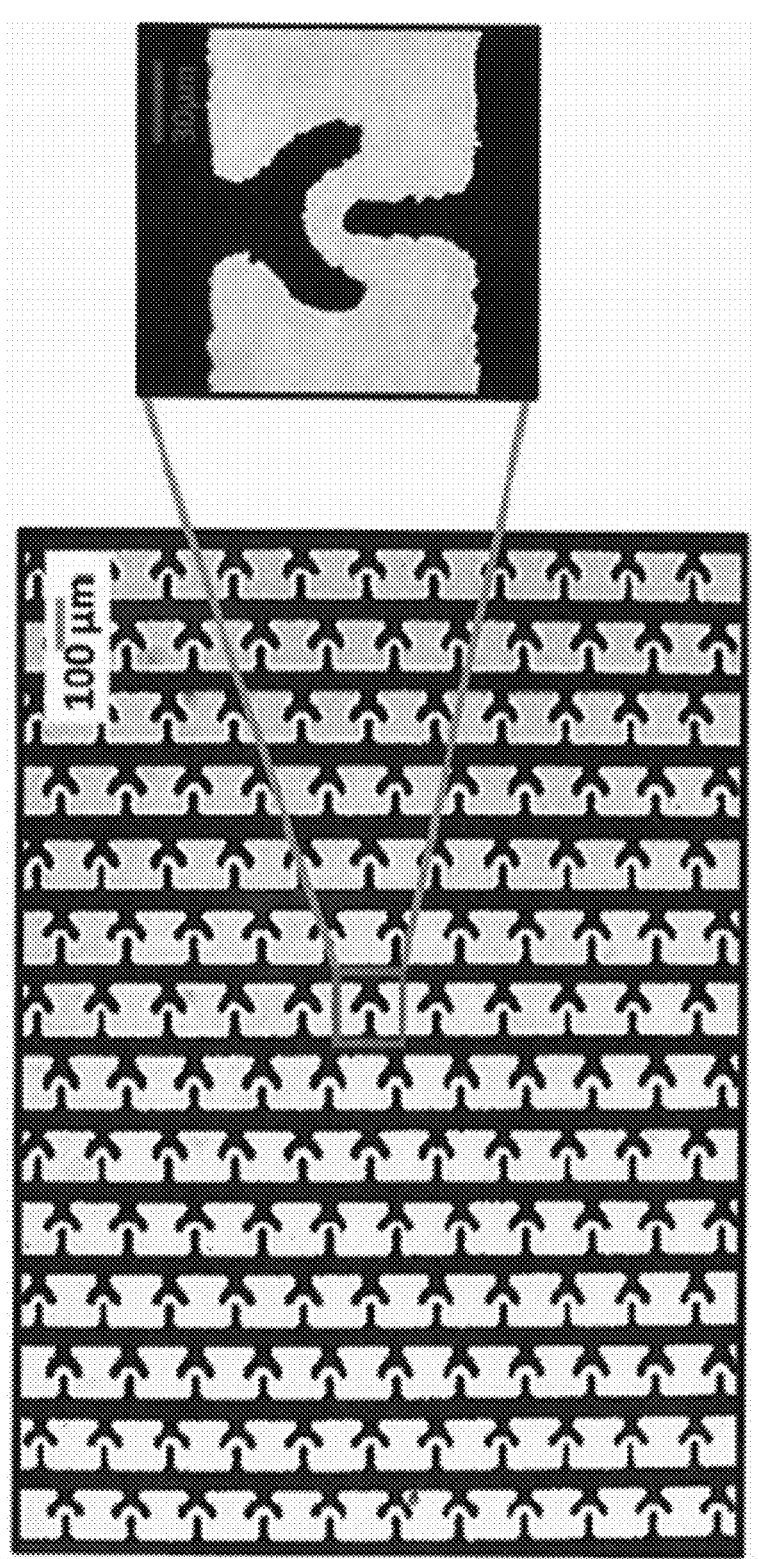
FIGS. 5A-C show the design and fabrication of DEP traps for T-cells. (A) Picture of an interdigitated T-trap electrode array with 20,000 single cell traps. Electrodes were fabricated in Au on glass substrate. (B) The calculated electric field distribution around electrodes. When T-cells trap using positive DEP, they will be trapped on the electrodes as single cells in A. When negative DEP is used, T-cells will be trapped in B. (C) Calculated electric field gradients around the electrodes. These electric field gradients generate high DEP forces on T-cells resulting in high-throughput trapping.
Figure 5C:
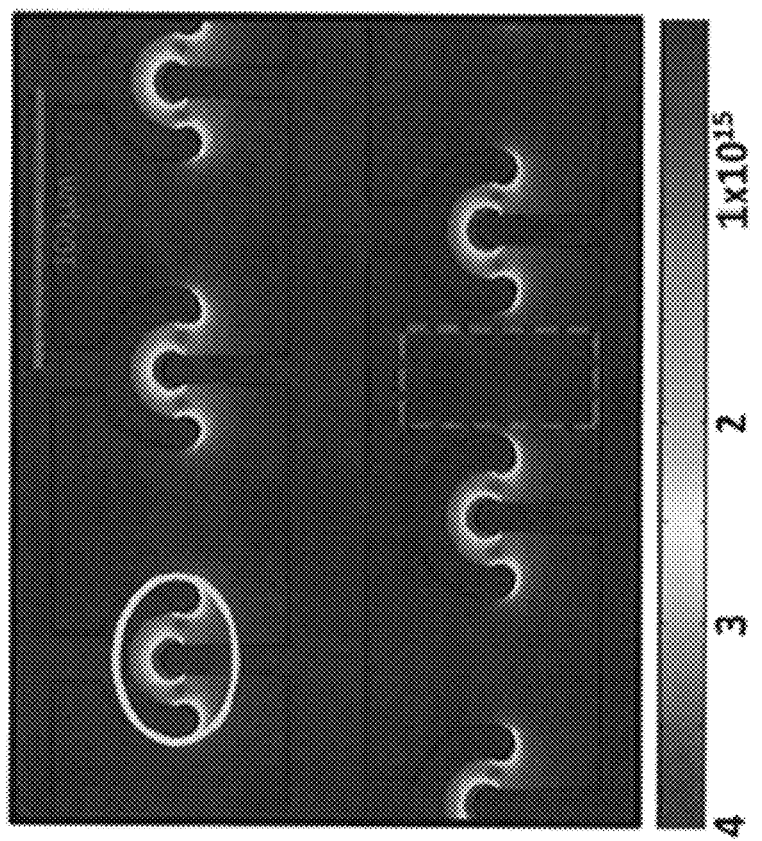
Figure 5B:
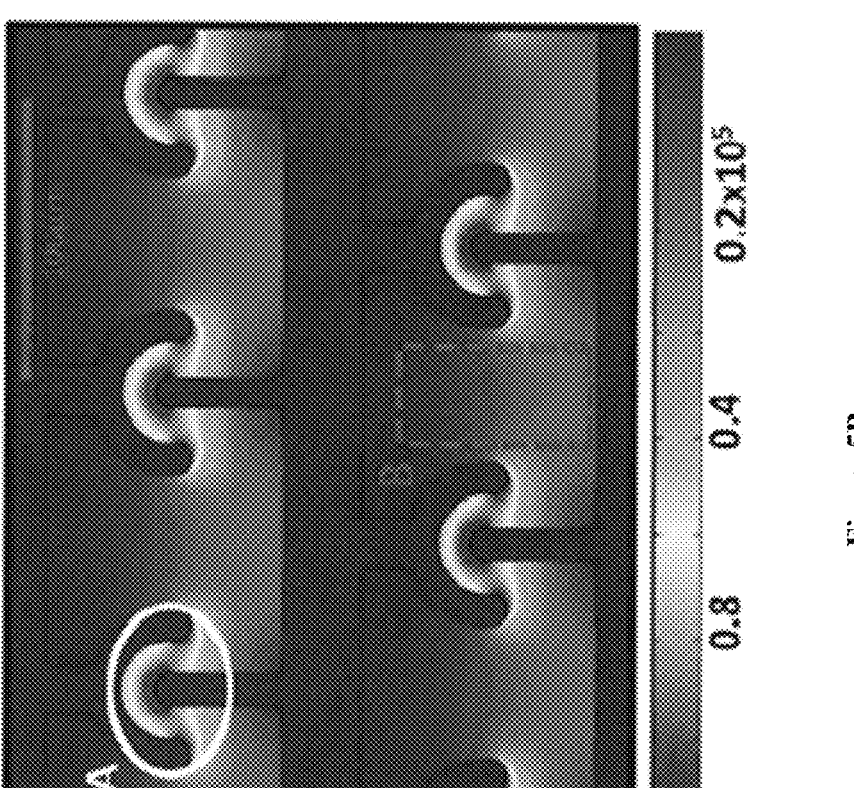

To successfully achieve this, a new class of electrodes that are capable of generating highly localized electric field gradients near electrodes to trap T-cells was designed (FIG. 5A). These electrodes are called T-traps, and a magnified view of a T-trap electrode is shown in FIG. 5A-inset. The instant inventors used the fabrication procedure utilized in fabricating IDEs. COMSOL software was then used to calculate the electric fields and electric field gradients that can be expected from T-traps. FIGS. 5B-C illustrate the calculated electric field (V/m) and field gradient (V$^2$/m$^3$) respectively. The electric fields and gradients highly localized between electrodes and T-traps are used to make T-cell patterns in well-defined locations. Spacing between patterns can be changed easily. There are two modes of patterning: T-cells can be patterned on the electrodes using positive DEP (white circle with A show the location of traps) or using negative DEP (red rectangle with B show the location).

In this Example, the device is utilized to study T-cell trapping. In particular, the external potential (peak to peak voltage required to generate electric field gradients), frequency, and conductivity of the buffer needed for trapping is determined. For each experimental condition, T-cells are trapped and free (non-trapping) T-cells are removed from the device. The DEP force is then turned off, the trapped cells are collected, and a cell count is performed. Using the T-cell counts, the percentage of trapped T-cells is calculated. The experimental condition that produces the maximum amount of trapping (that produces the maximum percentage-cells) is determined.

First, the conditions needed for expanding trapped T-cells by 100 fold are determined. T-cell expansion is a well-studied problem in the literature. A number of successful protocols have been developed to expand T-cells by 100-fold within about 10 days. In published studies, T-cells were expanded in static conditions where T-cells and other necessary reagents (antibodies) were placed in a stationary state in regular cell culture flasks/bioreactors. The instant inventors created a natural biological environment ex vivo in the device for T-cell expansion. By doing so there is faster expansion of T-cells. Briefly, using negative DEP, T-cells are placed as clusters with well-defined spacing. A flow of CD3$^+$/CD28$^+$ coated 5 µm diameter Dynabeads (Life technologies, Carlsbad, CA) is then applied around those clusters and the T-cell expansion is studied. The outlet of the device is designed to circulate or flow beads out of the device without flowing the expanding T-cells out of the device. The instant inventors studied the effects of the CD3+/CD28+ coated Dynabeads on the number of T-cells in clusters, the flow rate of the Dynabeads, and the ratio between T-cells and Dynabeads to achieve high-throughput expansion of T-cells. Finally, the optimum conditions for expanding T-cells in the instant device were determined, with these conditions believed to expand T-cells much faster than the static methods.

Next, the instant inventors performed experiments to study the DEP-based cell trapping. Commercially available fluorescent polystyrene beads (diameter=10 µm and green fluorescent protein on the surface) were patterned using negative DEP by applying a 10 kHz electric field. FIG. 6A illustrates the combined bright-field and fluorescent image showing locations of the traps with respect to T-trap electrodes. Note that clusters of beads are trapped near electrodes.

C2C12 cells were then suspended in 1×PBS buffer and flowed over the electrodes, an electric potential (10 Vpp and 200 kHz) was applied, and the cells were trapped on the electrodes. FIG. 6B shows a bright field image of trapped cells using negative DEP. The trapped cells are in the rectangle with white broken lines. In parallel, the T-cells were stained with Calcein AM (Thermo scientific) and trapped using positive DEP (10 Vpp and 50 kHz). FIG. 6C shows a fluorescent image of trapped cells. Trapped cells are inside the circles with white broken lines. Note that single cells are trapped using positive DEP and a cluster of cells is trapped with negative DEP. These results strongly support a more efficient method for expanding T-cells.

Figure 7A:
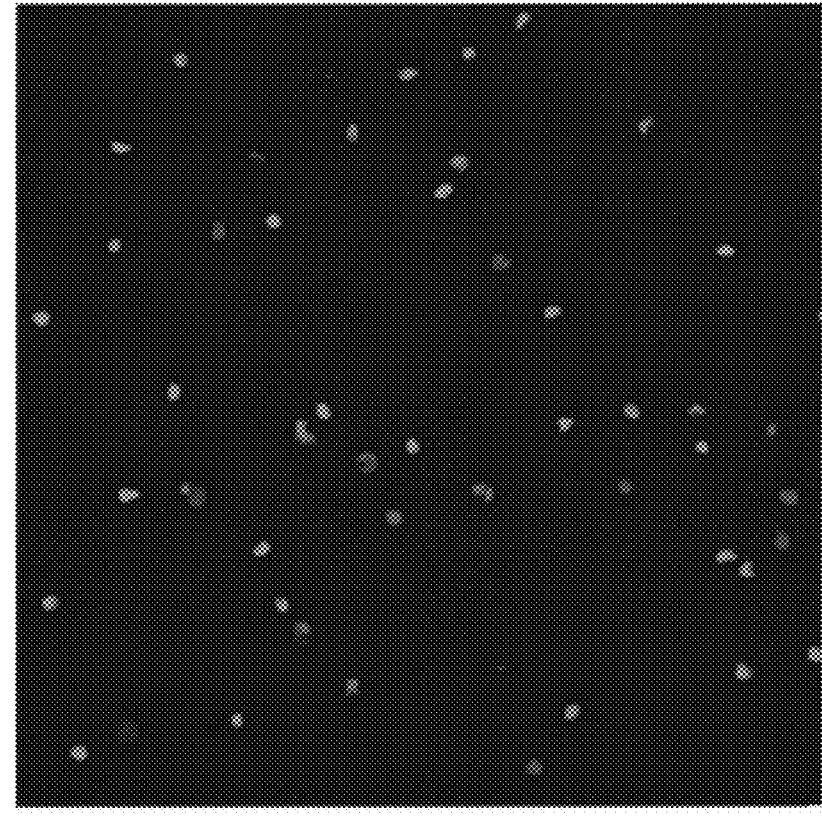
FIGS. 7A-B show transfection of cells with calcein A using electroporation. (A) Patterned cells collected after electroporation with calcein A. (B) Patterned cells collected after electroporation with calcein A and red dye.
Figure 7B:
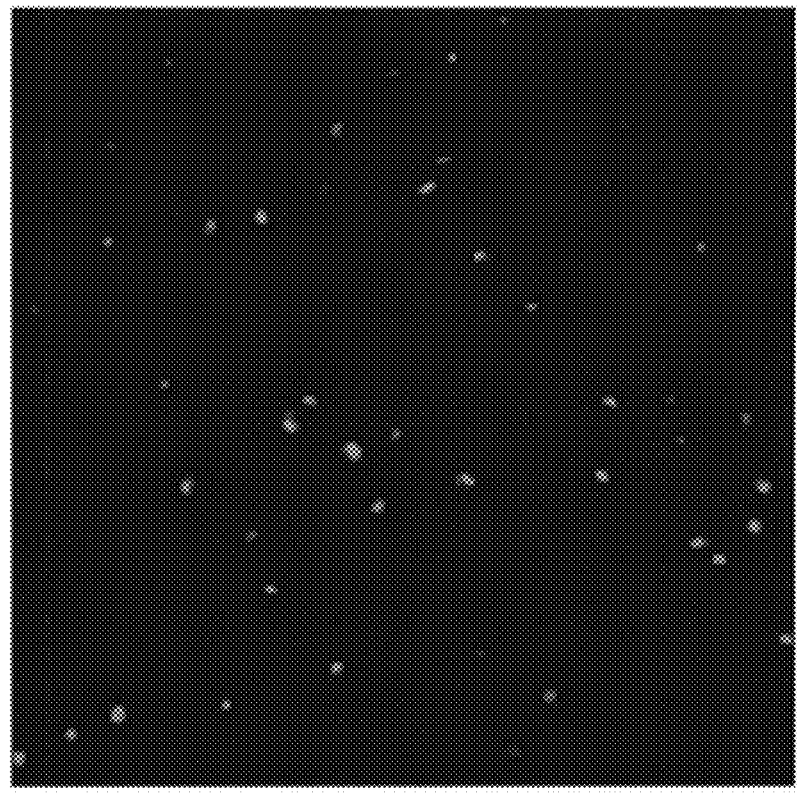

Example 4: Verification of Electroporation and Viability of Electroporated Cells To verify electroporation, cultured fibroblast cells were patterned as discussed above and then electroporated with calcein A, which is a labeled protein having a size of about 4-5 mg. After electroporation, the cells were collected. As shown by the fluorescence in FIGS. 7A-B, the labeled calcein A was electroporated into the cells. Although demonstrated with calcein A, these results are believed to be representative of electroporation with mRNA according to the instant disclosure.

Figure 8A:
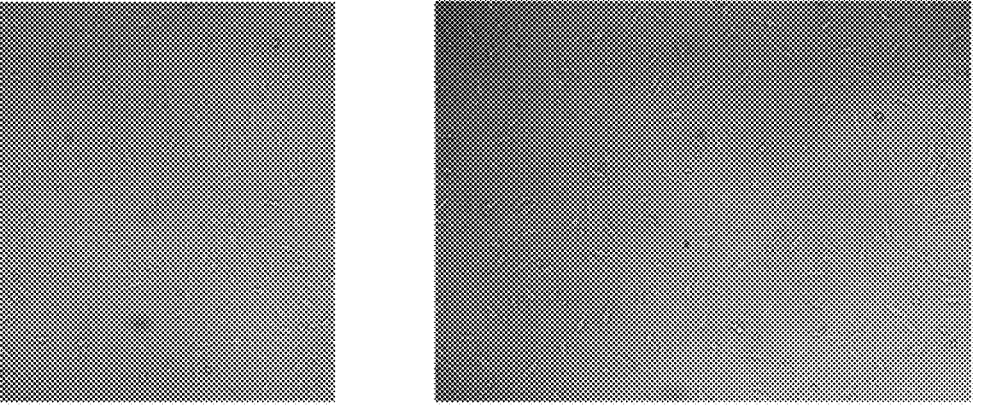
FIGS. 8A-B show images illustrating viability of cells after electroporation. (A) Growth of electroporated cells
Figure 8B:
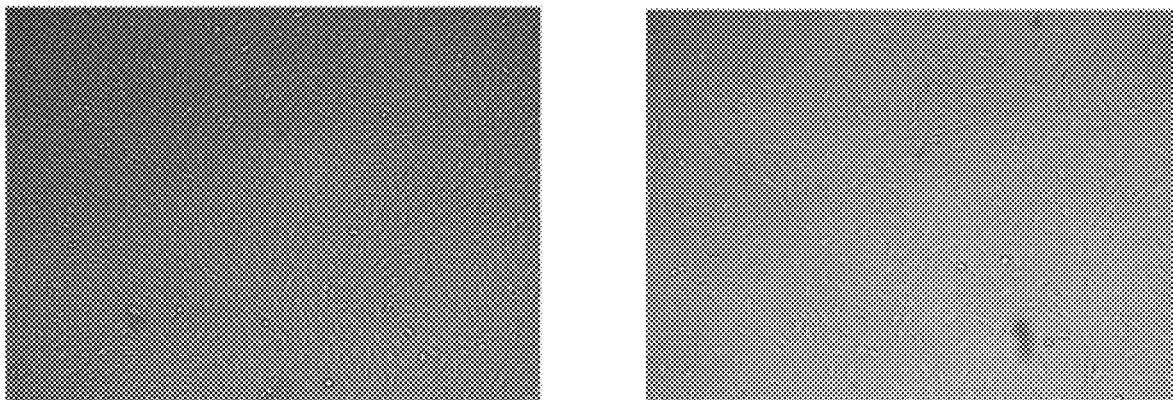

Next, the viability of the electroporated cells was verified through visual detection of cultured cell growth. More specifically, as illustrated in FIGS. 8A-B, the cultured cells demonstrated grown at both 24 hours (FIG. 8A) and 48 hours (FIG. 8B) post electroporation. Turning to FIGS. 9A-B, it was also demonstrated that the protein remained in the cells for at least 48 hours following electroporation.

Example 5: mRNA Coding for Proteins Targeting Cancer Cells

To demonstrate low-cost CAR-modified T-cell production without on-target/off-tumor toxicity, T-cells are manufactured to express ErbB2 (common target for cancer). Expression of ErbB2 has been used in the past but not as the result of the device or methods of the present disclosure. Green fluorescent protein (GFP) mRNA is used as the positive control and Anti-erbB2-scFv-CD28-OX40-CD3ζ mRNA targeting the production of ErbB2 immunoreceptors as the experiment. Each experiment involving T-cells is performed for CD4$^+$ and CD8$^+$ T-cells separately. First, the quantitative mRNA injection into T-cells through electroporation is studied, followed by the correlation between electroporation time and the average expression of immunoprotein in single T-cells (through fluorescence). Finally, the technology is scaled up to produce $10^7$ T-cells cost-effectively.

Example 6: Determine a Correlation Between Electroporation Time and Immunoreceptor Expression Level in T-Cells in Chamber 2

Although electroporation has been utilized to transfect T-cells with mRNA molecules, no study has focused on quantitatively transfecting T-cells with mRNA molecules. The objective of this example is to utilize electroporation for quantitative transfection of T-cells with mRNA molecules. As mentioned, there must be a dependence relationship between electroporation time and immunoreceptor expression. To demonstrate the feasibility, a relationship between electroporation time and expression level of immunoreceptor in single T-cells was determined. More specifically, T-cell patterning between IDEs was utilized and electroporation was performed on T-cells for a desired time. This provided a relationship between electroporation time and number of immunoreceptors on T-cells. The distribution of immunoreceptors on T-cells was also studied, using about $10^6$ T-cells per experiment.

Without wishing to be bound by theory, it is believed that when other conditions do not vary, the number of mRNA molecules transported into T-cells will depend on electroporation time. Since the expression levels of immunoreceptor molecules are proportional to the number of mRNA molecules, immunoreceptor expression level in T-cells can be controlled thorough the electroporation time.

Dielectrophoresis (DEP): The DEP is the movement of T-cells relative to the buffer, resulting from polarization forces produced by non-uniform AC (alternating current) electrical fields. Mathematically, the time-average DEP force acting on a T-cell in a non-uniform AC electric field can be represented by $$F_{DEP} = \tfrac{1}{2}\alpha\nabla(E^2) \tag{1}$$

where $\alpha$ is the polarizability of the T-cell, $\nabla$ is the vector operator, and E is the rms electric field, also known as the equivalent DC value.

$$\alpha = 4\pi\varepsilon_m r^3 \mathrm{Re}\{f_{CM}(\omega)\}, \tag{2}$$

where r is the radius of the T-cell, $\varepsilon_m$ is the suspending medium permittivity, co is the frequency of the applied electric field, and $\mathrm{Re}\{f_{CM}(\omega)\}$ is the real part of the Clausius-Mossotti factor is defined as $$f_{CM}(\omega) = (\varepsilon^*_p - \varepsilon^*_m)/(\varepsilon^*_p - 2\varepsilon^*_m) \tag{3}$$

where $\varepsilon^*_p$ is the complex permittivity of the T-cell and $\varepsilon^*_m$ is the complex permittivity of the suspending medium. The complex permittivity is given by $\varepsilon^* = \varepsilon - j(\sigma/\omega)$ with $\sigma$ the real conductivity, $\varepsilon$ the real permittivity and co is the frequency. The real part of the Clausius-Mossotti factor is theoretically bounded between $-\tfrac{1}{2}$ and 1, which determines the direction and the relative strength of the DEP force. If the magnitude of $\mathrm{Re}\{f_{CM}(\omega)\}$ is negative, then the T-cells move towards the lowest field strength region (negative DEP) and if it is positive T-cells are repelled from the lowest field strength region and move to regions of highest field strength (positive DEP).

FIG. 2 illustrates the basic steps of the production of CAR T-cells. FIGS. 10A-B show the purification of the expanded T-cells. The T-cells are trapped on IDE (micro-interdigitated electrodes) using DEP and wash away other materials such as beads and medium. Finally FIG. 10C shows the electroporation of patterned T-cells.

The magnitude of induced electric potential (electric field) in T-cell membranes determines the size of the pore that is used to transport exogenous mRNA molecules through electroporation. Therefore, to produce a homogenous mixture of T-cells transfected with mRNA molecules, it is required to have a uniform induced electric field in all T-cell membranes in the cell mixture. To experimentally achieve this, T-cells were first patterned as single files between parallel micro-electrodes so that every single T-cell will be subjected to the same external electric field. This was achieved utilizing micro-interdigitated electrodes (IDE) and T-cell patterning through the use of DEP. FIG. 11A illustrates the IDEs designed and fabricated for cell patterning/electroporation experiments. Standard lithography based microfabrication was used to fabricate IDE in Au on glass substrates. The space between electrodes was set to 30 μm to accommodate a single file of T-cells between electrodes.

Since the T-cell patterning is needed prior to electroporation, DEP based cell patterning on IDEs was demonstrated using commercially available polystyrene beads and C2C12 cells (mouse myoblast cells). The polystyrene beads were used in initial experiments as they are convenient to use and to find basic experimental conditions. The C2C12 and T-cells have identical dielectric properties and therefore C2C12 provide a good model to study T-cells. The process for DEP-based cell patterning is simple: first, cultured cells were suspended in standard 1×PBS buffer and about 500 μL of cells and buffer was pipetted onto the IDE electrode area.

An AC electric field (10 Vpp and 120 kHz) was applied and patterned the cells using negative DEP (FIGS. 11B-C). The frequency and magnitude of the electric field was then varied to achieve the successful T-cell patterning. Under these electric field conditions, more than 99% of the T-cells on the electrodes were patterned. Finally, the electric field (DEP) was turned off and it was observed that patterned T-cells neither move nor are disturbed.

It has been reported that about $1.25 \times 10^5$ V/m induced electric field in the T-cell membrane is required to electroporate T-cells. To study how T-cell patterning helps uniformly induce electric fields in each T-cell in a pattern, the induced electric fields on the membranes of every single T-cell that are in a pattern was calculated utilizing COMSOL software. In this calculation, a sample of 25 cells was used and a short DC electric pulse (1V) between IDEs was applied. FIG. 12C—red curve illustrates the induced electric fields on the membranes of patterned T-cells and the blue curve indicates the calculated induced electric fields of T-cells that are in traditional, commercially available electroporation equipment. By simple comparison, it is concluded that the proposed T-cell patterning based electroporation induces uniform electric fields in all T-cells and therefore all the T-cells will be transfected with equal amounts of mRNA molecules. In comparison, with current electroporation devices used in T-cell engineering (FIG. 12C—blue line), only about 20% of T-cells are electroporated with proper electric fields and 50% of T-cells are exposed to extremely high electric fields causing irreversible cell damage. Approximately 10% of cells are not electroporated at all. Out of 50% of T-cells that exposing to high electric fields, about 5-10% of T-cells will be viable. Therefore, T-cell viability number will be about 40% (20%+10%+5-10%). This agrees with published work by others.

A correlation between electroporation time and immunoreceptor expression level of single T-cells for GFP and ErbB2 mRNA molecules was determined by conducting the following experimental and theoretical studies:

Finding the frequency and the magnitude of the electric field needed for repeatable T-cell patterning between IDEs. The IDE array used in preliminary studies was used as the starting point of T-cell patterning. The instant inventors have demonstrated the successful cell patterning on IDEs using C2C12 cells (FIGS. 11A-C). Using these results as the basis, T-cells were patterned on IDEs. It has been reported that T-cells experience a large DEP around 100 kHz. Since the DEP force is utilized to pattern T-cells on IDEs, T-cell patterning began at 100 kHz and the patterning for 50-250 kHz in 50 kHz steps was studied. For each frequency, the number of T-cells in patterns as single files was studied between individual IDEs. The frequency that generates T-cell patterns with the highest number of T-cells was chosen. Additionally, the effect of T-cell concentration, magnitude of the electric field, physical gap between electrodes (30 μm), and conductivity of the T-cell medium on the T-cell patterning was studied. Each of these experimental conditions is studied separately to find the optimum experimental conditions (frequency, magnitude of the electric field, gap between individual IDE pairs) needed for a repeatable T-cells pattern with single file of T-cells between each IDE pair. Although it has been reported that exposure to low frequency electric fields/electric field gradients do not alter the cellular chemistry or cell viability, the instant inventors also studied the cell viability with the optimized experimental condition. The T-cell viability was studied using a commercially available assay kit (Cell Titer 96 ®, Promega, Madison, WI).

Determine the magnitude of the DC electric field needed to produce a homogenous mixture immunoreceptor expressing T-cells: According to the Nernst-Planck model, the mRNA transport into T-cells depends on the magnitude of the electric pulse (pulse height) that are applied for electroporation. In this example, the electroporation time is kept as a constant (pulse width ~5 ms, typical number in T-cell) and the mRNA transport is studied with the pulse height (magnitude of the DC field). Commercially available mRNA electroporation equipment (Genepulser Xcell, Munich, Germany) use $2 \times 10^5$ V/m (500V across electrodes separated by 4 mm). Therefore, the instant inventors use 0.5, 1, 1.5, 2, 2.5, 3 and $4 \times 10^5$ V/m to transfect T-cells with GFP mRNA molecules. Briefly, the T-cells are first patterned on IDEs using the experimental condition obtained above. The DEP is then turned off and DC pulses (indicated above) are applied for 5 ms. After each electroporation, a T-cell sample is collected and suspended in RPMI 1640 and incubated for 4-6 hours. The GFP expression is then measured through standard fluorescence activated cell sorting (FACS). The cell count vs. fluorescence intensity plotted and the distribution of the GFP in each T-cells sample produced from each electric field is analyzed. For each pulse height, the fluorescence vs. cell count is studied. Finally, the height of the DC pulse that produces the narrowest fluorescence width is determined. The condition that has the narrowest fluorescence width produces the homogenous mixture of T-cells with GFP expressions.

Determining a correlation between electroporation time and expression levels of immunoreceptors in T-cells. When all other electroporation conditions are optimized, according to the Nernst-Planck model, for a given initial concentration of mRNA molecules in the electroporation buffer, the electroporation time determines the number of mRNA transported into T-cells (FIG. 12B). The experimental conditions above may be used to find a correlation between electroporation time and expression of immunoreceptors in T-cells. First, about $10^6$ T-cells are patterned in the IDE array using the conditions obtained above. With 200 μg/mL of GFP mRNA molecules in the buffer, the DEP force is turned off and DC electric pulse obtained above is applied for ~5 ms for the IDEs array, and the T-cells are transfected with mRNA molecules. After the electroporation, T-cells are collected from the IDE array and suspended in RPMI 1640 media for 4-6 hours, followed by measurement of the mean fluorescence intensity (MFI) per T-cell. As the next step, the electroporation time is changed from 100 μs to 10 ms in 500 μs intervals and the mean fluorescence intensity (MFI) per T-cell is determined for each condition. After changing electroporation time, the MFI per T-cell is converted to number of GFP protein molecules using commercially available reagent kit (QIFIKIT, Dako, Carpinteria, CA). The electroporation time and expression of GFP molecules is then plotted to find a correlation. Finally the experiments are repeated using ErbB2 mRNA.

Accomplishment of the tasks in this Example generates knowledge on how T-cells interact with low frequency electric fields and produce electroporation. This knowledge is utilized to quantitatively inject mRNA molecules into T-cells to produce the required level of immunoreceptors, thereby accomplishing the objective of this aim.

When there is a large variation in expression levels of immunoreceptor from experiment to experiment, multiple regression analysis may be utilized to determine the correlation between electroporation time and the immunoreceptor expression level. Multiple regression analysis has been successfully utilized in similar studies (i.e. to analyze mRNA-protein relationships) by others and has been shown to be useful. Furthermore, if there is not T-cell patterning with DEP, electrophoresis-based T-cell pattering may be used. Starting with small electric fields (100 mV in 30 μm spacing IDEs), the optimum electric field needed for successful T-cell patterning is determined.

Example 7: Quantify the Dynamics of Tumor Cell Cytotoxicity and the Expression of Immunoreceptors in T-Cells in Chamber 2

Expression of immunoreceptors in T-cells is needed to lyse tumor-cells. Over-expression will increase the probability of the interaction between T-cells with healthy tissue cells, resulting in on-target/off-tumor toxicity. Therefore, it is required to find the minimum immunoreceptor expression level needs to be presented in T-cells to sufficiently lyse all target tumor cells. This will also be the safest level of immunoreceptor expression to minimize the on-target/off-tumor toxicity. This ability also leads into the study of the immunoreceptor expression dependent toxicity. This minimum level will depend on factors such as tumor type, stage, and the person. Once the minimum level of the immunoreceptors is determined, the production of T-cells with desired level of expression is performed.

This Example demonstrate the methodology used to find the minimum expression level of the immunoreceptor molecules in T-cells. These minimum expression levels may be used to develop a chart of minimum immunoreceptor molecules needed based on the tumor type, stage, age of the patient, etc., so that users can choose the appropriate values to produce T-cells. In addition, one can use the instant device to find the appropriate minimum expression level.

To successfully quantify the dynamics of tumor cell cytotoxicity and the expression of immunoreceptors in T-cells, when the electroporation has been completed, mRNA molecules that are in T-cells must freely scatter in the cytoplasm. The scattering of mRNA molecules is needed to avoid the unnecessary cross-hybridization between mRNA molecules. The cross hybridization may prevent the translation of mRNA molecules into immunoreceptors. Through calculations using the Nernst-Planck equation, the instant inventors have demonstrated that the mRNA molecules will indeed scatter in the cytoplasm (FIG. 12A). Therefore, it can be concluded that mRNA molecules that are transported into T-cells through electroporation will produce immunoreceptors on T-cell surfaces. Furthermore, the instant inventors have demonstrated that exposing mRNA molecules to low frequency electric fields (<150 kHz) and high electric field gradients ($\sim 10^{15}$ V/m$^2$) does not damage or alter the biological functionality.

Accordingly, the inventors next determined how to control the number of mRNA molecules that are transported into T-cells. Since the mRNA molecules are large (>4 kDa), it has been theoretically demonstrated that mRNA molecules will not efficiently transport into T-cells through simple diffusion. It has been experimentally observed that the transport mechanism is through electric field mediated diffusion (electro-diffusion). To fully understand this process, the Nernst-Planck equation was used to model the mRNA transport into a T-cell through electro-diffusion. It describes the motion of charged particles in fluid. Calculations were performed using COMSOL software and FIG. 12A illustrates the snap shots of the mRNA transport through electro-diffusion of an electroporated T-cell.

To understand the controlled mRNA transport into T-cells, the mRNA molecule transport into a single T-cell was studied with time. When time T=0 secs, the electroporation was started and counting the number of mRNA molecules that are being transported into the T-cell (with time) began (FIG. 12B). In this calculation, an initial mRNA molecule concentration of 200 μg/mL (typical concentration use to electroporate T-cells) was assumed. This mRNA concentration was used in current electroporation based T-cell production techniques. Through this calculation, it was demonstrated that there is a proportional relationship between the number of mRNA molecules that were transported into T-cells and the electroporation time. Therefore, by changing the initial mRNA concentration in the buffer and electroporation time, the number of mRNA molecules transported into T-cells can be precisely controlled. These results strongly support the belief that cytotoxicity of T-cells toward tumor cells will depend on the number of immunoreceptors expressed in T-cells.

Methods

Determining the minimum expression level of immunoreceptors to effectively lyse tumor cells. The ErbB2 mRNA molecules are injected into T-cells (CD8$^+$, about $10^6$ cells per run) by following the experimental conditions determined in Example 3. Briefly, 200 μg/mL ErbB2 mRNA molecules are used in the electroporation buffer and eight experiments are performed by changing the electroporation time (electroporation time=100, 250, 500, 750, 1000, 1500, 2000 and 3000 μs). Each experiment is repeated three times and the statistical significance is calculated. After electroporation, T-cells are collected and suspended in the RPMI 1640 separately and incubated for 4-6 hours to produce immunoreceptors. A cytotoxicity assay is then performed to analyze the transfected CD8$^+$-cells' ability to lyse target tumor cells. Commercially available human ovary cancer cells (SKOV3) are used as the target cells. It has been demonstrated that ErbB2 modified T-cells lyse SKOV3 cells. The cell lysis is accomplished using a commercially available kit (CellTrase CFSE kit, Thermo Fisher scientific). Briefly, T-cells transfected with mRNA molecules are activated using Muromonab-CD3 (OKT3, 100 ng/ml) and Interleukin-2 (IL-2, 400 U/ml) for two days. Tumor cells (ratio 1:2=SKOV3:T-cells (CD8$^+$)) are then added, incubate for 48 hours, and the proliferation assay is performed. The variation of the tumor cells' viability is calculated and compared with each electroporation time and the minimum electroporation time needed for lysing all tumor cells is determined. The electroporation time is converted to find the number of immunoreceptors needed in T-cells. This immunoreceptor level is called the "lytic threshold." Negative control experiments are performed using MDAMB 468 (ATCC, Manassas, VA) where no cell lysis is expected.

Determining the minimum expression level of immunoreceptors needed in T-cells to secrete cytokines. To determine minimum expression level needed to secrete cytokines, T-cell samples of CD4$^+$ and CD8$^+$ cells ($10^6$ cells) separately with ErbB2 mRNA molecules (200 μg/mL) were electroporated. For each T-cell type, the electroporation time is changed from 100, 250, 500, 750, 1000, 1500, 2000 and 3000 μs and eight samples were produced. Each T-cell type is mixed with SKOV3 (1:1 ratio 500000:500000 cells) and the mixture is incubated for 16-20 hours to study the cytokine release. It has been reported that 16-20 hours incubation will be sufficient to release cytokines. After incubation, the concentrations of common cytokines (interleukin 2 (IL-2), tumor necrosis factor (TNFα), and interferon-γ (IFNγ)) in ng/mL in each cell sample is determined using a commercially available cytokine assays kit and following the manufacturer's protocols (BD Biosciences). In parallel, T-cell samples (CD4$^+$ and CD8$^+$ cells) that did not undergo electroporation to transfect with ErbB2 are assayed. These experiments may be used as the negative control experiments.

The concentrations of IL-2, TNF$\alpha$ and IFN$\gamma$ are then compared in each T-cell sample produced using various electroporation times with the negative control. The analysis of variance (ANOVA) is used to compare the cytokine concentrations and determine the minimum electroporation time needed to secrete the cytokine. The electroporation time is converted to number immunoreceptors needed in T-cells (CD4$^+$ or CD8$^+$) to release cytokine molecules. This immunoreceptor level is called the "activating threshold."

in the method above, CD4$^+$ and CD8$^+$ cells are used separately, and the best option is selected and compared with the results for effective tumor cell lysing above.

Determining the minimum expression level of immunoreceptors needed to effectively lyse the target cells and release cytokines while minimizing the on target/off tumor toxicity. It has been reported that the lytic and activating thresholds have two different thresholds. Published studies involving lymphoblastic leukemia and chronic lymphocytic leukemia have reported that the activating threshold is a few thousand molecules (per T-cell) higher than the lytic threshold. Furthermore, it has been theorized that these threshold values are dependent on the tumor type, stage and the patient.

Here, these two threshold values are compared. These experiments were performed using the heterogeneous mixtures of immunoreceptor expressing T-cells and therefore true comparison between the two conditions is difficult and results may not be accurate. If the lytic threshold is greater than the activating threshold, the lytic threshold is used and the T-cells are electroporated to produce the immunoreceptor level that is equal to the lytic threshold. Alternatively, if the activating threshold is greater, T-cells are electroporated to produce the immunoreceptor level equal to the activating threshold. Since this is the minimum level of the immunoreceptors in T-cells to effectively eliminate the tumor cells, this is the safest level of immunoreceptor expression needed for proper efficacy. As the next step, the lytic and activating thresholds of two other ErbB2 positive tumor cells (breast cancer cells (MDA-MB-361) and lung cancer cells (A549)) are examined and studied. These cell-lines are purchased from ATCC (Manassas, VA) and cultured in the lab. The procedures developed are used to experimentally find the lytic and activating thresholds. This data is analyzed and conclusions may be made based on the tumor type.

This Example yields knowledge on the fundamental relationship between immunoreceptor expression and lytic/activating thresholds in a wide range of tumor cells. This knowledge is used to achieve the main objective of this Example.

Summarizing, it is clear from the foregoing that orientation of cell strands or sheets with respect to the direction of an external electric field is an important factor in maximizing efficacy of the production of induced transmembrane potential in cells. Cell-strands that are located parallel to the external electric field direction can significantly disturb the local electric fields near cells and suppress the induced transmembrane potential values, known as shadowing effect, which can result in significant variations of induced transmembrane potential values between individual cells take place. In contrast, external electric fields applied in the perpendicular direction to the cell strands more efficiently potentiate the induced membrane potential of cells. Therefore, producing cell strands or single-file cell orientation for each electrode provides a potential avenue for the production of controlled and tunable transfection of T-cells and other cell types with mRNA.

Example 8: Refine the Cell Alignment and Electroporation Parameters in Chamber 2

The studies described below, undertaken to maximize efficiency of the above-disclosed devices for controlled and tunable T-cell transfection, showed that interdigitated microelectrodes (IDE) used in chamber 2 to produce single-file T-cells patterns per electrode pair (one single file T-cell pattern per pair of electrodes) and subsequently electroporation of patterned T-cells by AC or DC electric fields applied perpendicular to the single file cells provided tunable and uniform electroporation of cells. It was considered important for tunable and uniform electroporation of all the cells in single file cell patterns that the single file cell patterns should locate in the uniform electric field regions produced by the interdigitated microelectrodes, and that the cells patterns should be produced between each electrode pair to expose the cells to uniform electric fields to eliminate the undesirable effects described above. Additionally, equal, uniform, and easily controllable DC pulse electric fields or AC electric fields could be produced across all the cells oriented in the single file patterns, enabling the ability to control the transfection level. Still more, no flow of cell sample to the microfluidics channel is required, which eliminates the degradation of cells and mRNA molecules.

After developing the two-electroporation device described above, further work was undertaken to examine how initial mRNA concentration, corresponding CAR expression in T-cells, and the cytotoxic lifespan of the manufactured CAR T-cells are inter-related. Additionally, a compartmental model of the T-cell cytoplasm was developed to theoretically study the translation of mRNA into CAR molecules. The results were used to understand the experimental results and to make predictions about the characteristics of mRNA-based CAR T-cells.

Methods

Interdigitated electrodes. Microscale interdigitated electrodes were manufactured on glass substrates. Traditional micro-fabrication methods such as photolithography, metal evaporation, lift-off, and dicing were utilized. Detailed protocols were as discussed above.

Electroporation device. First, microelectrodes with appropriate dimensions were manufactured. The dimensions of the electrodes are described below. Then Epoxy enclosures (approximate height 1 mm) with open tops were produced to concentrate the cell sample over the electrode array. No microfluidics pumps or syringes were used in the experiments.

Finite element modeling. (a) Design electrodes. COMSOL Multiphysics 5.3a (Burlington, MA) was used to design electrodes. To setup COMSOL simulations, briefly, interdigitated electrodes were drawn to scale using AutoCAD (Autodesk, San Rafael, CA) software, imported into COMSOL, and analyzed with the AC/DC electric current (EC) module. The frequency domain was used in simulations to incorporate the varying frequency studies. In all the analyses, buffer properties were set for 0.01×PBS (conductivity ($\sigma$)=0.03 S m-1, relative dielectric constant ($\varepsilon r$)=72). The electric potential, electric field, and electric field gradients were calculated and utilized to design the width of the electrodes and the spacing between individual electrodes. (b) Transmembrane potential. AC/DC module of COMSOL were developed to calculate the induced transmembrane potentials of T-cells. We used the shell model technique for this calculation, which allowed us to mimic the cell membrane. A cell membrane thickness of 0.5 nm was used in all calculations. Electric conductivity ($\sigma$) of 1.1 S m-1 and dielectric constant value ($\varepsilon_r$) of 71 for the T-cell cytoplasm were used. $\sigma$ and $\varepsilon_r$ values for cell membrane were 5×10-8 S m-1 and 13.55, respectively. An initial/resting transmembrane voltage of −70 mV was utilized across T-cell membranes.

T-cell isolation and culturing K-562 and SUP-B15 cells were performed according to previously published protocols.

Culturing Jurkat cells. The Jurkat cell line was received from Dr. Dorsam's group at North Dakota State University. Jurkat cells were cultured using a growth medium containing 89% RPMI 1640, 10% fetal bovine serum (FBS), and 1% penicillin/streptomycin in an incubator (5% $CO_2$ and 37° C.). Cells were passaged every two days during their log phase (at between 80-90% confluence) and used in experiments. To prepare cell samples for experiments, first cell sample was spun down at 500×g for 5 min. Then the cell sample was suspended in the electroporation buffer.

Preparation of the electroporation buffer. The electroporation buffer was 0.01×PBS with a conductivity of $\sigma$=0.03 S m-1, supplemented with sucrose to obtain an osmolarity of 180 mOsm L-1. To make the buffer, one part (by volume) of RNAse free 10×PBS (pH 7.4; Invitrogen, Carlsbad, CA) was mixed with 999 parts of RNAse free DI water (Invitrogen). Then, the osmolarity of the solution was adjusted to 180 mOsm L-1 using RNAse free D(+) sucrose.

Electroporation experiments. Upon isolation of T-cells from whole blood, they were suspended in StemCells® Easysep buffer (StemCellTechnologies, Cambridge, MA). T-cells were then spun down at 1200 rpm and re-suspended in electroporation buffer with a cell density of 1×106 cells per mL. mRNA molecules that produce EGFP were purchased (Biolegend, San Diego, CA) and CAR molecules against the CD19 antigen molecules on the ALL cells were commercially manufactured (G&P Biosciences, Santa Clara, CA). The fourth generation of CAR design was used to synthesis mRNA as it demonstrated complete remission for two-thirds of leukemia patients in the initial clinical trials. About 100 µL of the cell sample was added to the electrode, and experiments were conducted (patterning and electroporation) with the following conditions:
(1) P-DC: cells patterned with AC (sinusoidal) voltage (1 Vpp and 100 kHz, and 1 Vpp and 10 kHz) and transfected with 3 (0.5 ms per pulse) DC pulses of 9 Vp.
(2) P-AC: cells patterned with AC (sinusoidal) voltage (1 Vpp and 100 kHz, and 1 Vpp and 10 kHz) and transfected with sinusoidal voltage (8 Vpp and 100 Hz) for 150 ms.
(3) NP-DC: transfected with 3 DC pulses (0.5 ms per pulse) of 9 Vp and no-cell patterns were produced.
(4) NP-AC: transfected with sinusoidal voltage (8 Vpp and 100 Hz) for 150 ms and no cell patterns were produced.

Analysis of CAR (targeting CD19 antigen) expression. mRNA concentrations of 50, 25, and 5 µg mL$^{-1}$ with approximately 1×10$^5$ T-cells for each experiment were used in experiments. For each mRNA concentration, after patterning and electroporation experiments, about 3.9 mL of cell culture medium was added to the sample and divided into 10 equal volumes, pipetted to the 24-well plate (Falcon® 24-well clear flat bottom, Corning, NY) and incubated at 37° C. and 5% $CO_2$. The cell culture medium was composed of Iscove's modified Dulbecco's medium (IMDM) with 20% fetal bovine serum (FBS; ATCC, Manassas, VA) by volume and % IL2 (by volume; Miltenyi Biotec, Cambridge, MA). To evaluate the CD19 expression, a sample from a well was collected, mixed with 100 nM of Biotin-SP (long spacer) AffiniPure F(ab')$_2$ fragment goat anti-mouse IgG (Jackson ImmunoResearch Laboratories Inc., West Grove, PA) and incubated on ice (4° C.) for 25 minutes. Then the cells were washed with PBS, and 200 nM of FITC-streptavidin (Biolegend, San Diego, CA) was added, and the solution was mixed thoroughly. Next, the sample was incubated at room temperature for 5 minutes and then the cells were washed with PBS, and 100 nM of propidium iodide (P1; excitation: 493 nm, emission 636 nm; Thermo-Fisher, Waltham, MA) was added to analyze cell viability. Flow cytometry (fluorescence intensity vs. cell number) was performed, and the average fluorescence intensity and the cell viability of each sample were analyzed.

Cytotoxicity analysis. T-cells (~1×10$^5$) were electroporated (methods described above) with 50 µg mL$^{-1}$ of mRNA. After electroporation, about mL of medium (as described in the CAR analysis) was added and pipetted to 10 wells (equal volumes) in a 24 well plate. Then, 100 µL of the sample containing about 25 000 SUP B-15 cells was added to each well, and the cell mixture was incubated at 37° C. with 5% $CO_2$ (T cell:SUP B-15 ratio=3:1). The cells were taken out of the wells at specific time points, and each cell quantity was counted using flow cytometry. We used the forward-scattering and side-scattering feature of flow cytometry to count the SUP B-15 cell and T-cell populations. A similar procedure was used to analyze the cytotoxicity toward K-562 cells.

Mathematical modeling. A compartmental model was developed for the externally injected (by electroporation) mRNA to CAR (targeting CD19) translation in the cytoplasm of a T-cell. Definitions. R(t)=Externally injected mRNA concentration in a T-cell at time t; f(t)=Concentration of mRNA molecules in the cytoplasm of a T-cell injected by electroporation; $k_{d1}$=Rate of mRNA degradation in the cytoplasm of a T-cell; $k_{d2}$=Rate of CAR degradation in a T-cell; $k_{d3}$=Rate of CAR synthesis; p(t)=Concentration of CAR in a T-cell at time t; and $R_0$=Initial concentration (t=0) of mRNA in the cytoplasm. Assumptions: $k_{d1} > k_{d2}$.
Fundamental Equations.

$$\text{Accumulation} = \text{input} - \text{output} \tag{1}$$

$$\frac{dR(t)}{dt} = f(t) - k_{d1}R(t) \tag{2}$$

$$f(t) = R_0\delta(t) \tag{3}$$

$$\frac{dp(t)}{dt} = R(t)k_{d3} - p(t)k_{d2} \tag{4}$$

Solutions, $$R(t) = R_0 e^{-kd1t}u(t) \tag{5}$$

$$P(t) = R_0 k_{d3}\left(\frac{e^{-k_{d2}t} - e^{-k_{d1}t}}{k_{d1} - k_{d2}}\right)u(t) \tag{6}$$

Values, $k_{d1}$=12 days$^{-1}$, k=1 days$^{-1}$, $k_{d3}$=10000 pmol per day per pmol mRNA
Results and Discussion As discussed above, the electroporation devices used in experiments had interdigitated microelectrodes manufactured on glass substrates. Interdigitated microelectrodes are parallel electrode pairs that produce largely uniform electric fields, but near the electrodes, there can be some non-uniformity of electric fields or electric field gradient ($\nabla(E^2)$). Large number of biomedical assays, including cell separation, molecular concentration, and detection employ the dielectrophoretic (DEP) force produced using interdigitated electrodes. The magnitude of the DEP force is proportional to $\nabla(E^2)$. The DEP force is a valuable tool to develop biological assays because it can easily be produced using the microelectrodes, and the direction of the force is tunable to be toward the electrodes (attractive DEP force) or away from the electrodes (repulsive DEP force). In the present disclosure, DEP force was used to pattern T-cells as single files. For controlled and tunable transfection of T-cells with mRNA, one single file T-cell pattern per electrode pair was provided. Moreover, for a uniform electric field the single-file T-cell pattern was produced in the middle of the electrode pair.

We studied the possibility of using DEP force to produce one single-file T-cell pattern per electrode pair. Using the reported values for dielectric properties of cells such as the cytoplasmic conductivity and dielectric constant, and applied potential value of about 1 Vpp, we estimated the DEP force to be about 1 nN on T-cells. We have found that at least 1 nN DEP force is required to manipulate T-cells, i.e., hold cells between electrode pairs and produce single file T-cell patterns. Prior to experiments, we directly pipetted the cell sample that was suspended in the electroporation buffer on the electrodes. Subsequently, we studied the frequency dependent DEP force on T-cells by manually changing the frequency from 1 kHz to 1 MHz and the magnitude of the potential from 0.1-5 Vpp. We manually observed (using bright field or fluorescence microscopy) the attraction (attractive DEP force) or repulsion (repulsive DEP force) of T-cells by the DEP force. We found that at about 50 kHz, DEP force changes from repulsive to attractive. Strongest attractive and repulsive DEP forces were produced at 100 kHz and 10 kHz, respectively. After examining the frequency dependent DEP forces of T-cells, we used a combination of attractive and repulsive DEP forces to produce T-cells patterns. First, attractive DEP force (produced at 100 kHz) was used to pull the cells toward electrodes, and then repulsive DEP force (produced at 10 kHz) was used to push cells away from electrodes to the middle region between the electrodes. It was found that the use of attractive and repulsive forces was an efficient way to produce T-cell patterns with almost all T-cells in the sample. Repulsive DEP force alone could also be used but it was difficult to produce single file T-cells patterns with almost all T-cells in the sample. The T-cell viability after exposing to DEP forces was over 95%. The viability analysis was performed using commercially available Live/Dead assay kits (Life Technologies, Carlsbad, CA). T-Cell patterning using attractive and repulsive DEP forces took about 3 min to complete.

Figures 13A, 13B, 13C, 13D, 13E, 13F, 13G:
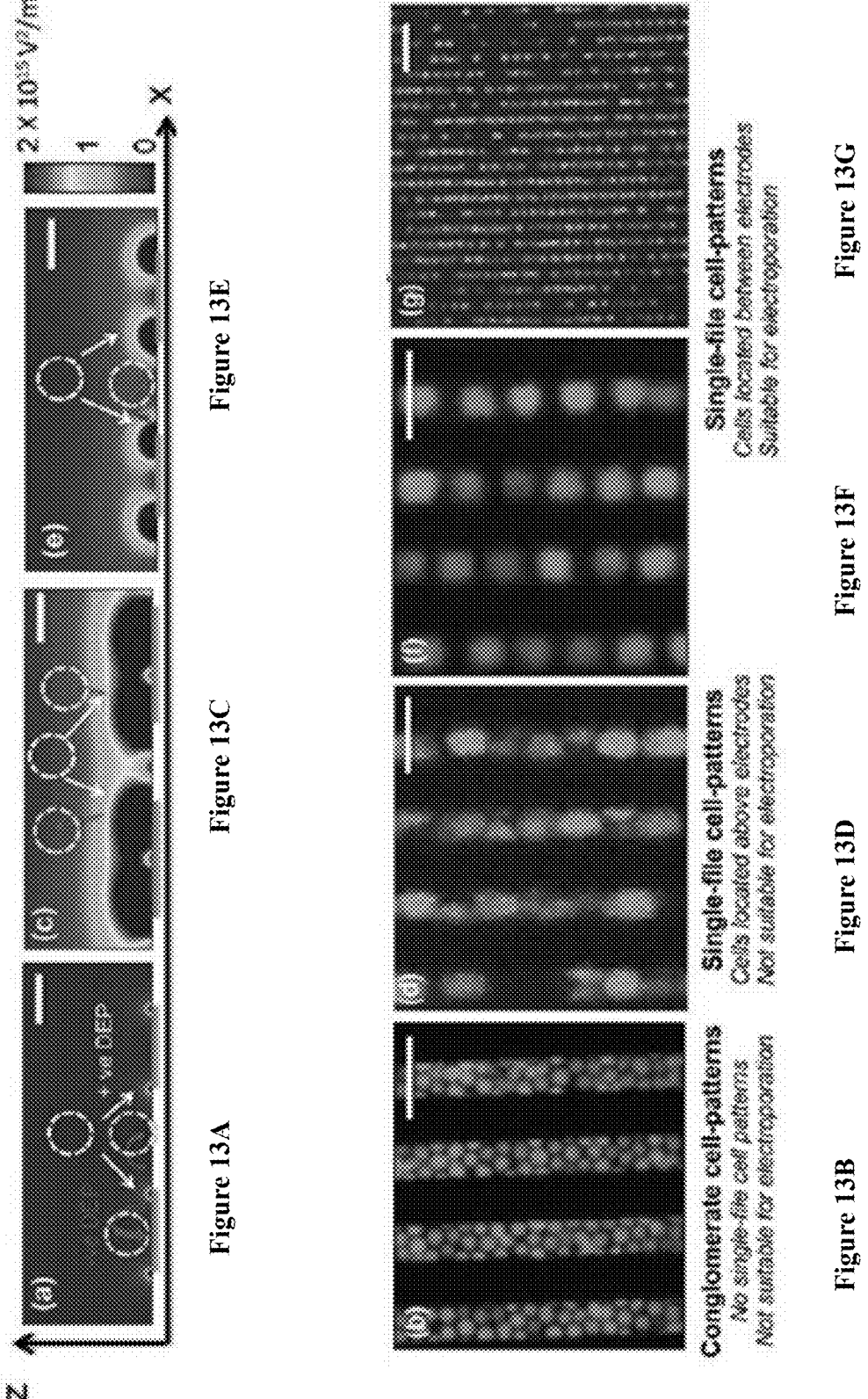

To minimize the shadowing effect discussed above, one single file T-cell pattern per pair of interdigitated electrodes is preferred. In addition, to expose every single-cell to tunable and uniform electric fields during electroporation, the single file cell pattern should be located between microelectrodes. During the initial experiments, we found that careful engineering of DEP force on the cells is required to produce desired cell patterns. For example, DEP force is directly proportional to $\nabla(E^2)$. The magnitude of $\nabla(E^2)$ depends on the geometrical parameters such as spacing between electrodes and width of the electrodes, and the magnitude of the applied potential. Moreover, the spacing between electrodes and width of the electrodes control the locations of highest and lowest $\nabla(E^2)$, and the magnitude of the applied electric potential contributes to the magnitude of $\nabla(E^2)$. To further understand how these variables contribute to produce desired cell patterns for electroporation experiments, we developed a series of finite element simulations and studied the impact of those variables. FIG. 13 summarizes our findings. We have calculated $\nabla(E^2)$ in FIGS. 13A, C, and E and S1. Approximate locations of the electrodes are indicated by solid orange lines. The circles with broken white lines show the locations of cells prior to applying attractive DEP force. White arrows show the travel path of a cell when attractive DEP is applied. The red arrows show the potential travel path of a cell when a repulsive DEP is applied. The circles with broken yellow lines show the locations where cell patterns are produced. First, we studied the cell-pattern formation when spacing between electrodes is significantly greater than the diameter of the cells. Cell diameter of 5 μm and spacing between electrodes value of 10 μm were used in the calculation. FIG. 13A shows the calculated $\nabla(E^2)$ values for the applied potential of 0.1 Vpp. Positive DEP force attracts the cells towards the highest $\nabla(E^2)$ or to the electrode edges. When the DEP force changed from attractive to repulsive, the cells concentrate on the locations that have the lowest $E^2$). Since the spacing between electrodes is significantly greater than the diameter of the cells, multiple single file cell patterns are produced. In addition, some cells can concentrate on the electrodes. The cells located on the electrodes may not electroporate to the same degree as the other cells located between electrodes. It is because cells located on the electrodes expose to low electric fields than other cells.

FIG. 13B shows an example of the cell patterns produced for the conditions discussed in FIG. 13A. We have used the electric potential of 0.1 Vpp and spacing between electrodes and the width of the electrodes are about 2-3 times of the cell diameter. Since there are conglomerate cell patterns are produced, as we explained earlier, these electrode dimensions and the potential are not suitable for electroporation experiments. FIG. 13C shows the $\nabla(E^2)$ produced by higher applied electric potential (5 Vpp) than the previous case (0.1 Vpp) and the spacing of the electrodes are approximately same size as the cell diameter and width of the electrodes (10 μm) are larger than the cell diameter (5 μm). For this electric potential, even with proper electrode dimensions, single file cell patterns are not useful for expected tunable and uniform electroporation as repulsive DEP forces push the cells away in the vertical direction from the electrodes. FIG. 13D shows the cell patterns produced under the conditions discussed in FIG. 13C. Note that each cell could be different vertical position above the electrodes, and each cell exposes to different electric field values during electroporation, which is not suitable for the proposed tunable and uniform electroporation. FIG. 13E illustrates ideal conditions needed to produce desired single-cell pattern between electrodes. We have used the electric potential of 1 Vpp and electrode dimensions (width and spacing between electrodes were about 5-7 μm) are approximately equal to the cell diameter (5 μm). Electric potential value and electrode dimensions are sufficient to produce the largest $\nabla(E^2)$ and attractive DEP force near electrodes and smallest $\nabla(E^2)$ or repulsive DEP force between electrodes. FIG. 13F shows a picture of the single file cell patterns produced using the conditions discussed in FIG. 13E. In addition, we have also investigated another case (data not shown), where an electric potential of 1 Vpp is applied, but the width of the electrodes (15 μm) is larger than the cell diameter (5 μm) and spacing between the electrodes are approximately same size as the cell diameter. When repulsive DEP force is applied, some cells could go over the electrodes, and other cells concentrate between electrodes. As described earlier, the cells located on the electrodes may not electroporate to the same degree as the other cells located between electrodes. Therefore, this design is also not suitable for producing the desired single-file cell pattern. We did not experimentally produce any cell patterns with these conditions.

Figure 1:
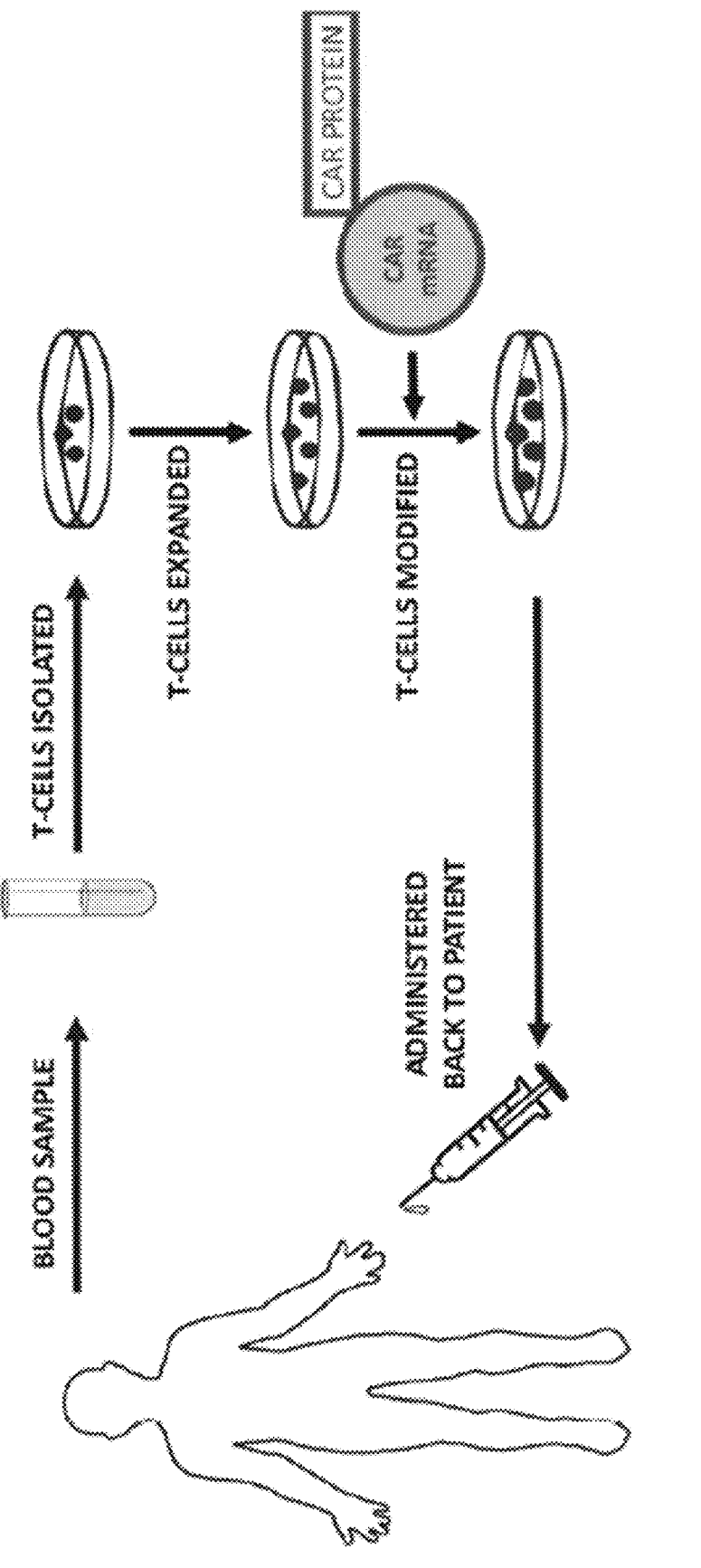
FIG. 1 shows the present method for performing CAR T-cell Therapy.

In the experiments shown in FIGS. 13B, D and F, we used cultured Jurkat cells, as they closely resemble T-cells. After designing electrodes and optimizing the electric potentials, we switched to using primary T-cells isolated from whole blood samples and performed T-cell patterning experiments (FIG. 1G). The single file T-cell patterns illustrated in FIG. 1(g) contain a single file of T-cells between individual electrodes. Cell samples with $10^6$ cells per mL were used in the cell patterns shown in FIG. 1G. We found that, depending on the cell diameter, proper dimensions for spacing between individual electrodes, width of the electrodes, and the electric potential, is needed to produce desired single file cell patterns. Moreover, the spacing between electrodes and the width of the electrodes needed to be approximately 1.5 times the cell diameter. For example, an electrode spacing of 10 μm and an electrode width of 10 μm were needed to pattern T-cells (~7 μm) in the electrode array. Generally, we have found that, for smaller cells (e.g., T-cells with diameter ~7 μm) suspended in low conductivity buffer (e.g., 0.03 S m$^{-1}$), 1 Vpp potential is sufficient.

Once the cells are patterned as single files between electrodes, electroporation was used to transfect cells with mRNA molecules. It has previously been demonstrated that a threshold value of 1 V for the induced transmembrane potential is needed to initiate the electroporation. Above 1 V, the resealing capability decreases, and subsequently, significant damages to the cell take place. This evidence demonstrates the importance of the induced transmembrane potentials. Moreover, nearly 1 V is needed to electroporate cells without cell damage or harming cell viability. We calculated the induced transmembrane potentials on patterned cells (with DEP force) and randomly placed cells (no DEP force used).

FIG. 14 shows the isometric view of randomly placed cells, including the locations of each cell and the calculated induced transmembrane electric potential values. Note that some cells are placed on the electrodes (e.g., FIGS. 14A, B, and C), and some other cells are located between electrodes (e.g., FIGS. 14D and E). For further comparison, in the figure right below FIG. 14A, we calculated the induced transmembrane electric potential values of the randomly placed cells, FIGS. 14B and C illustrate cell locations and the calculated induced transmembrane electric potentials of two single file cell patterns. The figure right below FIGS. 14B and C shows the induced transmembrane electric potentials of each cell. Next we extracted the maximum values of the induced transmembrane electric potential values of each cell. Also, we extended our analysis and calculated the maximum induced transmembrane electric potential values of the cells that were placed in traditional cuvette-based electroporation devices that use macro electrodes (FIG. 14D). The largest variation in the maximum induced transmembrane electric potential of 1.40±1.2 V was calculated for the macro electrode-based cuvette electroporation. 1 V induced transmembrane potential with the smallest variation was calculated for patterned cells in microelectrodes (1±0.05 V), and randomly placed cells in the microelectrodes had an induced transmembrane potential of 1.05±0.2 V. By comparison of calculated induced membrane electric potential values of each case, patterned cells with microelectrodes have almost identical induced transmembrane potential values. Therefore, all the patterned T-cells could uniformly transfect with mRNA. In addition, mRNA levels in T-cells could be varied by simply varying the external electric potential.

To further understand the potential benefits of the electroporation of cells with micro- vs. macro-electrodes, we further extended our FEM simulation and calculated induced transmembrane electric potential values of cells placed between micro- and macro-electrodes (FIG. 14E). Typically, dimensions of the macro electrodes (in cm) are significantly greater than the diameter of the cells (in μm), and micro-electrodes and cells have dimensions in μm. Therefore, induced transmembrane potentials are produced locally in the cell membrane by the microelectrodes, while macro electrodes induce electric potentials in the entire half-spherical space of the cell (FIG. 14E). As noted above, when we utilized electroporation with microelectrodes, we found very high cell viability values (~100%). In addition, as the localized induced transmembrane potential of 1 V produced by microelectrodes does not cause significant irreversible cell damage, longer electroporation times could be used for the cells in microelectrodes. Longer electroporation times could be useful for transfecting cells with high or tunable levels of mRNA molecules. In contrast, macro-electrodes induce electric potentials with considerable variability, and therefore low cell viability and uneven (or low) transfection efficiency is expected.

We employed AC and DC electric fields in the electroporation experiments. FIG. 15 shows the proposed two-step electroporation method. FIG. 15A shows a picture of the device that we used for experiments. FIG. 15B shows the fluorescence image (excitation: 493 nm, emission: 636 nm) of the patterned T-cells. Note there was no visible fluorescence was recorded after making cell patterns. FIG. 15C illustrates the image of the cell sample after electroporation by DC pulses. T-cells were transfected with commercially available PI. Rectangle drawn with broken line shows a patterned and transfected single-file of T-cells. After transfection, cells were collected by pipetting and stained with calcein molecules (ThermoFisher) and re-patterned. The calcein molecules enter into the live cells and produce strong florescence (excitation: 495 nm, emission: 515 nm). FIG. 15D shows the image of the transfected and stained T-cells. T-cells with yellow shows the transfected viable cells. The rectangle drawn with broken line illustrates a single-file of T-cells. T-cell patterns shown in FIGS. 15C and D were produced using $10^5$ cells per mL.

We then examined the impact of T-cell patterning followed by electroporation on the transfection efficiency and cell viability. We calculated the transfection efficiency by quantifying the percentage of cells in sample that has measurable levels of protein expression (e.g., EGFP and CAR). These experiments were conducted on primary T-cells isolated from commercially available pooled whole blood samples of healthy individuals (Innovative Research, Novi, MI). For our initial experiments, we used commercially available mRNA molecules that produced enhanced green fluorescent protein (EGFP; TriLink Biotechnologies, San Diego, CA.; excitation: 488 nm, emission: 509 nm). EGFP is a common target used to quantify the transfection levels of T-cells. FIG. 16A illustrates the transfection efficiency values for patterned and electroporated with AC and DC potentials, and randomly placed and electroporated with AC and DC potentials. We used commercially available flow cytometry (BD; Franklin Lakes, NJ) to measure the EGFP expression of the transfected cells. The transfection efficiency of the patterned and electroporated (AC electric fields) cells at 24 h was about 50%, which is more than two times that of the randomly placed T-cells (23.8%). These values for patterned and electroporated with DC and randomly placed and electroporated with DC pulses were 50.8% and 26.2%, respectively. We have also found that transfection efficiency could be further increased by re-mixing T-cells, followed by re-patterning and electroporation (data not shown). The cell viability was analyzed after 24 h of electroporation.

Commercially available live/dead assays (Millipore-Sigma, Burlington, MA) were used to measure the percentage of live cells. Patterned and electroporated cells with DC potential had average cell viability values of 85.5%. Randomly placed and electroporated cells with DC potentials had average cell viability values of 70.6%. Similarly, patterned and electroporated with AC potentials and randomly placed and electroporated with AC potentials had average cell viability values of 82.6% and 74.5%, respectively. As stated earlier, the difference in viability of patterned vs. randomly placed cell could be attributed to the induced membrane potentials produced by these methods. The transfection efficiency and cell viability values of two-step electroporation of primary T-cells is therefore better than reported traditional DC electroporation methods and comparable with reported flow through electroporation devices.

Regardless of the electroporation method or where T-cells were located (patterned or randomly placed), almost all the samples produced their highest EGFP expression after 24 h of electroporation (FIG. 16A). This shows that T-cells will take about 24 h to translate the majority of mRNA to EGFP. After the 24 h time point, the transfection efficiency was decreased. This decrease in EGFP expression could result from cell division or degradation of EGFP molecules. As the transfected cell divides, daughter cells may take up mRNA molecules from mother cells, and therefore a gradual decrease in the expression is expected. However, the division of primary T-cells is a complex process, and T-cell division under standard culture conditions may not be very effective. Therefore, we assumed that the number of T-cells is constant during the evaluation period.

To further understand the time-dependent degradation of GFP expression, we examined the maximum fluorescence intensity, which provides information about the maximum number of EGFP molecules expressed at any time point (FIG. 16B). Patterned and electroporated T-cells produced the highest maximum fluorescence intensity values peaking at 24 h. We assumed that maximum fluorescence intensity, could be proportional to the number of mRNA molecules injected into those cells at t=0. Therefore, by comparison, patterned and electroporated cells could have a higher quantity of mRNA molecules than randomly placed and electroporated cells. The maximum EGFP intensity drastically decreases for all 4 cases after the 24 h time point. Maximum EGFP expression at any given time after 24 h is also proportional to the maximum EGFP intensity at 24 h. By combining the two observations, we could conclude that the initial quantity of mRNA present in T-cells determine the maximum value of EGFP and the lifespan of the EGFP expression. The lifespan of EGFR is defined as the period (after transfection at t=0) at which measurable (by flow cytometry) EGFP is present.

We then conducted CAR T-cell manufacturing experiments using the mRNA molecules that produce CARs that recognize the CD19 antigen on ALL cells. We selected the CD19 and ALL cells because CAR T-cell therapy is currently approved for treating ALL. Since the patterned and electroporated T-cells with AC and DC electric fields produced identical cell viability and transfection efficiency (FIG. 16A), we used AC electric fields alone for the rest of the study. First, we examined how transfected T-cells with mRNA produced CAR molecules. FIG. 17A shows the time-dependent CAR expression (average expression per cell) in T-cells for different concentrations of mRNA. We only varied the mRNA concentration between experiments and kept all other experimental parameters (such as electroporation time and frequency of the electric field) unchanged. The CAR expression peaked earlier than that for EGFP molecules (24 h for CD19 and 48 h for EGFP), which shows that peaking time is dependent on the mRNA type. According to FIG. 17A, the magnitude of the peak value of CAR is dependent on the mRNA concentration in the buffer. Therefore, magnitude of peak CAR expression proportional to the initial mRNAs levels in the T-cells at t=0. This data also demonstrates that lifespan of CAR expression in T-cells is proportional to the peak expression value at 24 h. The time point at which peaking of CAR occurs is independent of the mRNA concentration. Furthermore, CAR expression lasted over 10 days for the 50 μg mL$^{-1}$ mRNA concentration. The duration of CAR expression in T-cells manufactured by our method is longer (over 10 days) than other reported studies by Birkholz et al. (5 days), Zhao et al, (4 days), Pohl-Guimaraes et al. (7 days), and Boissel et al. (2 days).

Our findings on EGFP and CAR expressions are valuable information for broadly understanding the translation of mRNA to protein expression. Moreover, in the context of CAR T-cells, a lower decay rate is desirable for CAR molecules because sustained. CAR expression could be beneficial for producing longer duration of targeted cytotoxicity. Furthermore, our findings could also be useful for manufacturing CAR T-cells with pre-determined lifespans of cytotoxicity. For example, one can produce highly active CAR T-cells (T-cells with very high CAR expression) or moderately active CAR T-cells (T-cells with low CAR expression) for desired time periods by changing the initial mRNA molarity in the electroporation buffer. In addition to mRNA molarity in the buffer, changing other experimental variables such as electroporation time will also be used to vary the transfection levels of mRNA in T-cells. To further improve our understanding about the CAR expression with time, we developed a compartment modelling approach (FIG. 18) to study the time-dependent CAR expression from externally injected mRNA by electroporation. The model utilized the mRNA degradation, protein degradation, and translation of mRNA to protein as variables.

The schematic diagram of FIG. 18 illustrates how mRNA molecules translate to CAR molecules in T-cells. We assumed that there was no CAR expression at t=0, and mRNA was injected as a bolus input (eqn (3)) at t=0 by electroporation. This assumption based on the fact that the electroporation time (in ms) was significantly smaller than the CAR expression time (in days). Two fundamental equations (eqn (2) and (4)) were derived by assuming conservation of molecules (eqn (1)) in the cytoplasm of a T-cell. Eqn (2) and (4) were solved analytically and results were used to derive analytical expressions for the time-dependent variation of mRNA (eqn (5)) and CD19 (eqn (6)).

We used the study published by Hargrove et al. to obtain numerical values for $k_{d1}$, $k_{d2}$, and $k_{d3}$. However, degradation of CAR without target cells could be significantly less, and therefore we assumed a value of 1 per day for the rate of degradation. First, we studied how the initial mRNA level modulates the lifespan of the CAR expression or time-dependent expression of CAR in T-cells (FIG. 17B). We calculated the CAR expression for the initial mRNA levels
($R_0$) of 1, 10, and 25 (a. u). The data show that the lifespan
of the CAR is proportional to the initial mRNA levels ($R_0$).
Additionally, the maximum level of CAR expression (or
peak value of CAR expression) is also proportional to the
initial mRNA levels. Surprisingly, the half-life of CAR
expression does not change with $R_0$. The half-life is defined
as the time taking to achieve 50% reduction of the maximum
expression of CAR. The model and the experimental data
predict that the time point at which CAR peaking is inde-
pendent of the mRNA concentration. These conclusions
from the mathematical model agree with the experimental
observations for CAR that target CD 19 antigen. By com-
paring experimental data with mathematical modeling we
can conclude that CAR expression, peak value for CAR, and
the lifespan of CAR expression could be modulated by
varying the initial m RNA concentration in T-cells.

To further understand the characteristics of CAR T-cells
manufactured in the two-step electroporation process, we
examined the time-dependent variation of CAR expression
when target cancer cells were present. We used the com-
mercially available ALL cells (SUP-B15 cell line) that
express the CD19 antigens as target cells. Briefly, we
electroporated T-cells with mRNA, suspended both the
electroporated T-cells and SUP-B15 cells (T-cell:SUP-B15
ratio=4:1), and co-cultured in an incubator (37° C.; 5%
$CO_2$). We did not change any parameters in the protocol that
we used to manufacture CAR T-cells in FIG. 17A. FIG. 19A
shows the normalized temporal variation of average CAR
per T-cell with and without ALL. By comparison, when
SUB-B15 cells are present, the time taken for CAR expres-
sion to peak occurred earlier than for the case without
SUP-B15 cells (8 h vs. 22 h; FIG. 19A. We used the
developed mathematical model to predict the CAR expres-
sion in the presence of SUP-B15. We systematically
increased the numerical values of $k_{d2}$ from 1 to 11 and
calculated the CAR expression (FIG. 7(b)). Our calculation
shows that the peak value of CD19 appears earlier when
target cells are present, which is in agreement with our
experimental data. Moreover, by comparison of the time
values (both experimental- and modeling-based), it can be
concluded that CAR expression degrades about 10 times
faster when the target cells are present.

Next, we evaluated the manufactured CAR T-cells' ability
to kill or be cytotoxic towards target cancer cells. Birkholz
et al. demonstrated that mRNA-based CAR T-cells manu-
factured to target breast cancer cells through ErbB2 and
CEA receptors have successfully lysed ErbB2$^+$ and CEA$^+$
tumor cells. In addition, a similar study has reported that
mRNA-based CAR T-cells exhibited cytolytic activities that
are similar to viral-based CAR T-cells. Furthermore, Birk-
holz et al. demonstrated that the percentage lysis of cancer
cells (target cells) is dependent on the ratio of target cells to
CAR T-cells. Moreover, the higher the target:effector ratio,
the higher the cell lysis percentage reported. As explained
earlier, we manufactured CAR T-cells that recognize the
CD19 antigens. We used the commercially available SUP-
B15 cell line, which is ALL. Briefly, we co-cultured CAR
T-cells and SUP-B15 cells (SUP-B15:CAR T-cells=11:4) in
a standard 96-well plate. The number of CAR T-cells and
SUP-B15 cells at each time point was quantified with flow
cytometry. FIG. 20 illustrates the variation of SUP-B15 cell
quantity with time for electroporated (both patterned and
randomly placed) cells. The number of CAR T-cells was
almost constant during the evaluation period (data not
shown). Data presented in FIG. 20 show that CAR T-cells
manufactured by patterning and electroporation kill cells faster than the cells electroporated without patterning. This
may be because patterned and electroporated cells could
have higher CAR molecules than randomly placed and
electroporated cells. The presence of a large number of CAR
molecules enhances the probability of finding the CD19
antigen molecules on ALLs. Birkholz et at demonstrated that
a target:effector cell ratio of 1:2 produced only 2% cell lysis
at 24 h when CAR T-cells manufactured with a commer-
cially available electroporation system were used. In com-
parison, CAR T-cells manufactured by patterned and elec-
troporated cells produced about 60% cell lysis at 24 h. Cells
electroporated without patterning had about 25% cell lysis at
24 h. These cell lysis percentages reflected the T-cell trans-
fection by macro- vs. microelectrodes and patterned vs.
randomly placed cells. Negative control experiments were
performed by electroporating patterned T-cells without
mRNA. We found that the SUP-B15 cell population
increased by approximately 200% during the 7-day evalu-
ation period (data not shown).

We then investigated the cytotoxicity of CAR T-cells
toward other leukemia cells (chronic myelogenous leuke-
mia, K-562) that do not have any known expression of CD19
antigen molecules. The CAR T-cell:K-562 ratio was 4:1.
FIG. 21 compares the variation of K-562 and SUP-B15 cells
during the presence of CAR T-cells that express CD19. We
found CART-cells manufactured by electroporation (both
patterned and randomly placed) did not produce a significant
reduction of K-562 cell numbers. We have also found that
different reduction rates for SUP-1315. Moreover, in the first
20 h, about 60% of SUP-B15 cells were killed, and then only
38% of SUP-B15 cells were killed in the next 100 h, and
finally, about 1% of SUP-B15 cells were killed in the last 25
h. As we discussed earlier, this could be representative of the
probability of conjugating CAR molecules (T-cells) and
CD19 antigen (ALL). As SUP-B15 reduces, the probability
of conjugation could also reduce.

CONCLUSIONS

The present disclosure demonstrates that initial mRNA
levels in T-cells modulated the peak value of target CAR
expression, expression time, and lifespan of cytotoxicity. We
have also found that half life of CAR expression does not
vary with initial mRNA content. In addition, two-step elec-
troporation substantially increased the cell viability and
transfection efficiency of the T-cells. Ideally, higher trans-
fection efficiency is needed to produce a sufficient number of
CAR T-cells from a small amount of a patient's blood
sample. Similarly, when there are CAR T-cells with long
cytotoxic lifespans, a small number of CAR T-cells or a
small amount of whole blood could be used for therapy. The
cell viability after electroporation is also a critical factor
because the removal of dead and dying cells is challenging.
This is because there are no known T-cell surface antigens
that we can utilize to purify dead or dying cells. The
presence of non-viable cells in the CAR T-cell sample is
very undesirable because these cells could produce serious
side effects. To this end, our group recently demonstrated
that dielectrophoretic cell separation could be utilized to
purify T-cells in a label-free manner after electroporation.

We did not see a difference in maximum EGFP or CAR
expression or lifespan of EGFP or CAR expression in T-cells
manufactured with AC (100 Hz) and DC electric fields.
However, studies have demonstrated that cell transfection
rates from AC electroporation (in the kHz range) can be
significantly higher than traditional DC electroporation. The
oscillating AC electric fields produce a mild sonication effect on molecules, which reduces molecular crowding near the pores and increases the transfection rate. We also investigated the high-frequency (>1 kHz) AC electroporation and found that T-cells are difficult to electroporate at high frequencies. This could result from the low induced membrane potentials (<1 V) at high frequencies. Studies conducted by Chang et al. showed that they were able to electroporate and transfect red blood cells at higher frequencies (>1 kHz) when high frequency electric fields were integrated with DC pulses. Furthermore, it is highly unlikely that the low frequency electric fields (100 Hz) that we used in experiments could produce sonication effects on mRNA molecules. Generally, sonication effects are produced by either electrophoresis or dielectrophoresis. The electrophoresis is vanishingly small with AC electric fields. The dielectrophoresis produced in low frequency values (~100 Hz) for mRNA molecules is also very small because we found earlier that mRNA molecules require AC fields with 100 kHz or more to produce substantial dielectrophoresis effect.

The CAR T-cells manufactured by our device expressed CARs that lasted for more than 10 days. From a therapeutic standpoint, longer cytotoxic lifespans are desired to avoid frequent infusions, as this drives up the cost and discomfort for the patient. On the other hand, to address the personalized therapeutic needs, CAR T-cells with tunable cytotoxicity would be of great benefit and might mitigate undesirable effects of multiple infusions. Our findings suggest that the initial CAR expression level in T-cells could dictate the lifespan of cytotoxicity. To increase the lifespan of cytotoxicity, one potential approach would be to increase the initial T-cell mRNA concentration. Although it is simple to increase the initial mRNA concentration in the electroporation buffer, it is counterproductive. This is because increased mRNA concentrations lead to molecular crowding near the pores and reduce transfection efficiency. Increasing the electroporation time or membrane potential will improve transfection efficiency, but these activities significantly reduce cell viability. As discussed earlier, our device/technique has produced high transfection rate and cell viability. Therefore, this device/technique could be used to further investigate the possibility of manufacturing CAR T-cells with significantly longer cytotoxic lifespans or even CAR T-cells with tunable lifespans.

Prior studies have suggested that about $10^6$ CAR T-cells per kg of the patient is required for efficacious therapy. Therefore, up to $80 \times 10^6$ CAR T-cell manufacturing capacity is required to treat most individuals. We are therefore investigating scaling up of the two-step electroporation described herein to apply our device in treatments. Based on the current cell electroporation capacity of the device described herein, to accommodate the need of most individuals (up to 80 kg in weight), we estimate that a suitably scaled-up device could be a size of 6" wafer.

What is claimed is:

1. A device to produce modified T-cells including heterologous nucleic acid molecules, comprising
    a first chamber for proliferating a population of T-cells and
    a second chamber for modifying the T-cells to express a desired T-cell chimeric antigen receptor,
    wherein the first chamber comprises a plurality of electrically conductive micro-trap structures adapted to guide and concentrate T-cells by application of a non-uniform electric field and the second chamber comprises a plurality of interdigitated electrodes adapted to pattern the T-cells between electrodes and to electroporate the T-cells.

2. The device according to claim 1, wherein the first chamber and the second chamber each comprise a top surface, a bottom surface and four side surfaces, wherein the top surface and the bottom surface are substantially parallel to one another and are disposed at a spaced distance of about 100 μm.

3. The device according to claim 2, wherein two of the four side surfaces are disposed essentially parallel to each other and define ends of the device, and another two side surfaces are disposed essentially parallel to each other and define sides of the device.

4. The device according to claim 3, wherein one or both ends of the device have openings.

5. The device according to claim 2, wherein the top surface and the side surfaces are made of polymethylsiloxane (PDMS) and the bottom surface is made of glass.

6. The device according to claim 1, wherein the first chamber plurality of structures consists of a series of T-shaped electrodes termed T-traps.

7. The device according to claim 1, wherein the second chamber plurality of interdigitated electrodes each comprises one or more channels bordered on each side by a first metal electrode and a second metal electrode, wherein the first metal electrode is connected to a first polarity of an electric function generator and the second metal electrode is connected to a second polarity of the electric function generator to allow an electrical potential to flow between the first metal electrode and the second metal electrode.

8. The device according to claim 7, wherein the metal is selected from the group consisting of gold (Au), silver (Ag), platinum (Pt), copper (Cu), iron (Fe), aluminum (Al), Tin (Sn), Nickel (Ni), Carbon (C), doped silicon (Si), indium tin oxide (ITO), or an alloy of metals.

9. The device according to claim 8, wherein the metal is selected from the group consisting of Au, Ag, Pt and ITO.

10. The device according to claim 7, wherein each of the plurality of interdigitated electrodes is adapted to pattern the T-cells and to achieve electroporation of the T-cells by application of a suitable electrical potential.

11. The device according to claim 10, wherein the T-cells are patterned by applying a suitable electrical potential sufficient to orient the T-cells in a single file.

12. The device according to claim 11, wherein the suitable electrical potential is from about 20 mV to about 500 mV.

13. The device according to claim 12, wherein the suitable electrical potential is about 100 mV.

14. The device according to claim 11, wherein the electroporation is achieved by application of a Direct Current Pulse (DCP) at a current strength of about 1.5V/P.

15. The device according to claim 14, wherein the DCP is applied at a pulse of from about 1 ms to about 10 ms.

16. The device according to claim 15, wherein the DCP is applied at a pulse of about 5 ms.

17. The device according to claim 1, wherein the strength of the non-uniform electrical potential in the first chamber is about 100 mV.

18. The device according to claim 1, wherein the space between electrodes is about 30 μm.

19. A kit comprising the device according to claim 1, combined with one or more accessories selected from the group consisting of syringes, nutrients, food, antibody-coated beads, cytokines, buffers, storage containers, transfer vehicles and instructions.

20. A device to produce cells modified by incorporation of heterologous nucleic acids, comprising:

a first chamber adapted for proliferating a population of the cells, the first chamber comprising a plurality of electrically conductive micro-trap structures adapted to guide and concentrate cells by application of a non-uniform electric field sufficient to induce dielectrophoresis; and a second chamber adapted for modifying the cells to express a desired antigen receptor, the second chamber comprising one or more interdigitated electrodes adapted to pattern a plurality of cells into a single file orientation between paired electrodes of the one or more interdigitated electrodes.

21. The device according to claim 20, wherein the first chamber plurality of structures consists of a series of T-shaped electrodes termed T-traps.

22. The device according to claim 20, wherein the one or more interdigitated electrodes are adapted to pattern the cells by application of an electrical potential sufficient to induce a positive or a repulsive dielectrophoretic force; and wherein the one or more interdigitated electrodes are further adapted to achieve electroporation of the cells by application of a direct current pulse (DCP) or an alternating current pulse (ACP) across the interdigitated electrodes and interposed plurality of cells.

23. The device according to claim 22, wherein each of the one or more interdigitated electrodes is defined by first and second electrodes disposed at a spaced distance from one another, wherein the first electrode is connected to a first polarity of an electric function generator and the second electrode is connected to a second polarity of an electric function generator to produce an electrical potential flowing therebetween.

24. The device according to claim 23, wherein the spaced distance is from about 1 to about 1.5 times the diameter of the cells of the population of cells.

25. The device according to claim 23, wherein the electrical potential used to pattern the cells is from about 10 m Vpp to about 10Vpp.

26. The device according to claim 25, wherein the electrical potential used to pattern the cells is about 1 Vpp.

27. The device according to claim 23, wherein the strength of the ACP is about 8 Vpp.

28. The device according to claim 22, wherein the strength of the DCP is from about 0.75 to about 1.5V.

29. The device according to claim 28, wherein the DCP is applied as one or more pulses each having a duration of from about 1 ns to about 10 ms.

30. The device according to claim 29, wherein the DCP is applied as one or more pulses each having a duration of about 5 ms.

31. The device according to claim 20, wherein a strength of the non-uniform electrical potential in the first chamber is about 100 mV.

32. The device according to claim 20, wherein the cells are T-cells and the modified cells are chimeric antigen receptor (CAR) T-cells.

* * * * *